US006517838B1

(12) United States Patent
Höök et al.

(10) Patent No.: US 6,517,838 B1
(45) Date of Patent: Feb. 11, 2003

(54) DECORIN BINDING PROTEIN ESSENTIAL PEPTIDES AND METHODS OF USE

(75) Inventors: Magnus A. Höök, Houston, TX (US); Eric L. Brown, Bellaire, TX (US)

(73) Assignee: The Texas A&M University System, College Station, TX (US)

( * ) Notice: Subject to any disclaimer, the term of this patent is extended or adjusted under 35 U.S.C. 154(b) by 159 days.

(21) Appl. No.: 09/596,120

(22) Filed: Jun. 16, 2000

(51) Int. Cl.[7] .................................................. A61K 39/00

(52) U.S. Cl. .................................. 424/185.1; 424/184.1; 424/234.1; 424/130.1; 530/324; 435/7.2

(58) Field of Search .................... 425/183.1; 424/184.1, 424/130.1, 234.1; 435/7.2; 530/324

(56) References Cited

U.S. PATENT DOCUMENTS 5,853,987 A * 12/1998 Guo et al.

FOREIGN PATENT DOCUMENTS

| | | |
|---|---|---|
| DE | 196 32 862 A | 2/1998 |
| WO | WO 97 27301 | 7/1997 |

OTHER PUBLICATIONS

Cassatt, D., et al. "DbpA but not OspA is expressed by *B. borgdorferi* during spirochetemia and is a target for protective antibodies." (1998), *Inf. Immun.* 66:5379–5387.

International Search Report. (Dec. 21, 2000), PCT.

Schaible, U.E., M.D. Kramer, K. Eichmann, M. Modolell, C. Museteanu, and M.M. Simon, "Monoclonal antibodies specific for the outer surface protein A (OspA) of *Borrelia burgdorferi* prevent Lyme borreliosis in severe combined immunodeficiency (scid) mice," (1990), *Proc. Natl. Acad. Sci., U.S.A.* 87:3768–3772.

Hanson, M.S., D.R. Cassatt, B.P. Guo, N.K. Patel, M.P. McCarthy, D.W. Dorward, and M. Höök, "Active and passive immunity against *Borrelia burgdorferi* decorin binding protein A (DbpA) protects against infection," (1998), *Infect. Immun.* 66:2143–2153.

Guo, B.P., E.L. Brown, D.W. Dorward, L.C. Rosenberg, and M. Höök, "Decorin binding adhesins from *Borrelia burgdorferi*," (1998), *Mol. Miro.* 30:711–723.

Guo, B., S.J. Norris, L.C. Rosenberg, and M. Höök, "Adherence of *Borrelia burgdoferi* to the proteoglycan decorin," (1995), *Infect. Immun.* 63:3467–3472.

Roberts, W.C., B.A. Mullikin, R. Lathigra, and M.S. Hanson, "Molecular analysis of sequence heterogeneity among genes encoding decorin binding proteins A and B of *Borrelia burgdorferi* sensu lato," (1998), *Infect. Immun.* 66:5275–5285.

Brown, E.L., B.P., Guo, P. O'Neal, and M. Höök, "Adherence of *Borrelia burgdorferi*: Identification of critical lysine residues in DbpA required for decorin binding," (1999), *J. Biol. Chem.* 274:26272–26278.

Pride, M.W., E.L. Brown, L.C. Stephens, J.J. Killion, S.J. Norris, and M.L. Kripke, "Specific Thl cell lines that confer protective immunity against experimental *Borrelia burgdorferi* infection in mice," (1998), J. *Leukoc. Biol.* 63:542–549.

(List continued on next page.)

*Primary Examiner*—Lynette R. F. Smith
*Assistant Examiner*—Ginny Allen Portner
(74) *Attorney, Agent, or Firm*—Howrey Simon Arnold & White

(57) ABSTRACT

*Borrelia burgdorferi,* the causative agent of Lyme disease, expresses on its surface a decorin binding protein, DbpA and DbpB. Lysine residues necessary for DbpA binding to decorin and DbpA peptides containing these critical residues essential for decorin binding are disclosed. It is further disclosed that vaccination using peptides incorporating these critical binding domains of DbpA can confer a delayed-type hypersensitivity response to DbpA and reduce the number of *B. burgdorferi* organisms present in infected animals.

3 Claims, 10 Drawing Sheets

1 65
MIKCNNKTFNNLLKLTILVNLLISCGLTGATKIKLESSAKAIVDEIDAIKKKAASMGVNFDAFKD

MIKCNNKTFNNLLKLTILVNLLISC[P1]

LLISCGLTGATKIKLESSAKAIVD[P2]

AIVDEIDAIKKKAASMGVNFDAFKD[P3]

66 182 125
KKTGSGVSENPFILEAKVRATTVAEKFVIAIEEEATKLKETGSSGEFSAMYDLMFEVSKP

DAFKDKKTGSGVSENPFILEAKVRA[P4]

AKVRATTVAEKFVIAIEEEATKLKE[P5]

TKLKETGSSGEFSAMYDLMFEVSKP[P6]

126 163 170 187
LQELGIQEMTKTVSMAAEENPPTTAQGVLEIAKKMREKLQRVHKKNQDTLKKKNTEDSTAKS

EVSKPLQELGIQEMTKTVSMAAEEN[P7]

AAEENPPTTAQGVLEIAKKMREKLQ[P8]

REKLQRVHKKNQDTLKKKNTEDSTAKS[P9]

OTHER PUBLICATIONS

Keane–Myers, A., and S.P. Nickell, T cell subset–dependent modulation of immunity to *Borrelia burgdorferi* in mice, (1995), *J. Immunol.* 154:1770–1776.

Lengl–Janssen, B., A.F. Strauss, A.C. Steere, and T. Kamradt, "The T helper cell response in Lyme arthritis: Differential recognition of *Borrelia burgdorferi* outer surface protein A in patients with treatment–resistant or treatment––responsive Lyme arthritis" (1994), *J. Exp. Med.* 180:2069–2078.

Rao, T.D., and A.B. Frey, "Protective resistance to experimental *Borrelia burgdorferi* infection of mice by adoptive transfer of a CD4+ T cell clone"(1995)k *Cell. Immunol.* 162:225–234.

Schaible, U.E., M.D. Kramer, R. Wallich, T. Tran, and M.M. Simon "Experimental *Borrelia burgdorferi* infection inbred mouse strains: andbody response and association of H–2 genes with resistance and susceptibility to development of arthritis" (1991), *Eur. J. Immunol.* 21:2397–2405.

Zeidner, N., M. Dreitz, D. Belasco, and D. Fish, "Suppression of acute Ixodes scalpularis–induced *Borrelia burgdoferi* infection using tumor necrosis factor–α, interleukin–2, and interferon–γ" (1996), *J. Infec. Dis.* 173:187–195.

Zeidner, N., M.L. Mbow, M. Dolan, R. Massung, E. Baca, and J. Piesman, "Effects of *Ixodes scapularis* and *Borrelia burgdorferi* on modulation of the host immune response: induction of a TH2 cytokine response in Lyme disease–susceptible (C3H/HeJ) mice but not in disease–resistant (Balb/c) mice" (1997), *Infect. Immun.* 65:3100–3106.

* cited by examiner 1 65
MIKCNNKTFNNLLKLTILVNLLISCGLTGATKIKLESSAKAIVDEIDAIKKKAASMGVNFDAFKD

MIKCNNKTFNNLLKLTILVNLLISC[P1]

LLISCGLTGATKIKLESSAKAIVD[P2]

AIVDEIDAIKKKAASMGVNFDAFKD[P3]

66 182 125
KKTGSGVSENPFILEAKVRATTVAEKFVIAIEEEATKLKETGSSGEFSAMYDLMFEVSKP

DAFKDKKTGSGVSENPFILEAKVRA[P4]

AKVRATTVAEKFVIAIEEEATKLKE[P5]

TKLKETGSSGEFSAMYDLMFEVSKP[P6]

126 163 170 187
LQELGIQEMTKTVSMAAEENPPTTAQGVLEIAKKMREKLQRVHKKNQDTLKKKNTEDSTAKS

EVSKPLQELGIQEMTKTVSMAAEEN[P7]

AAEENPPTTAQGVLEIAKKMREKLQ[P8]

REKLQRVHKKNQDTLKKKNTEDSTAKS[P9]

FIGURE 1

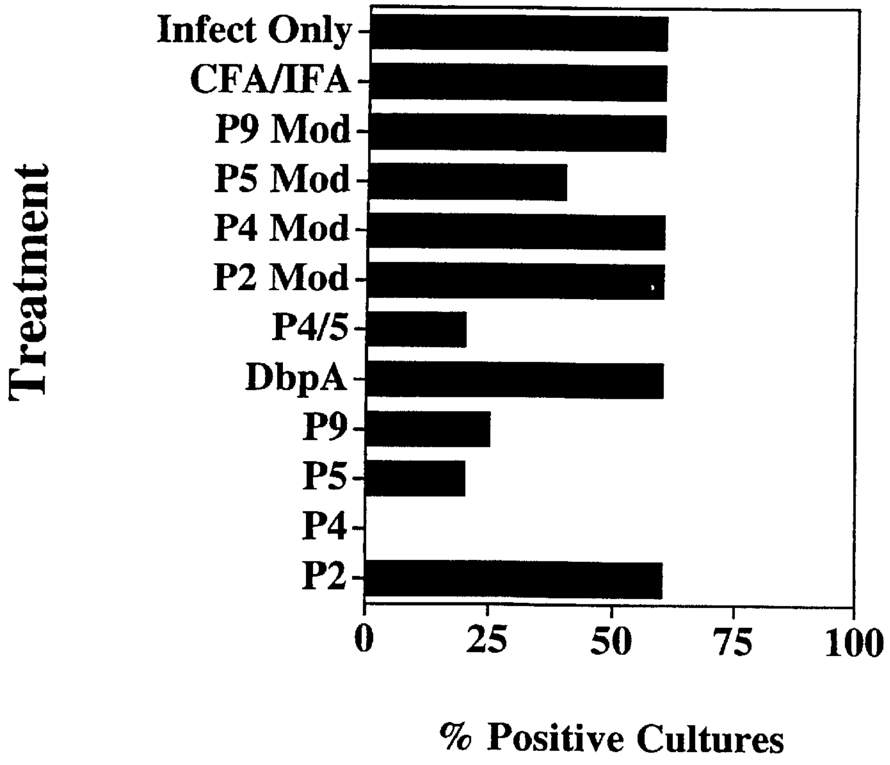
FIGURE 5-A

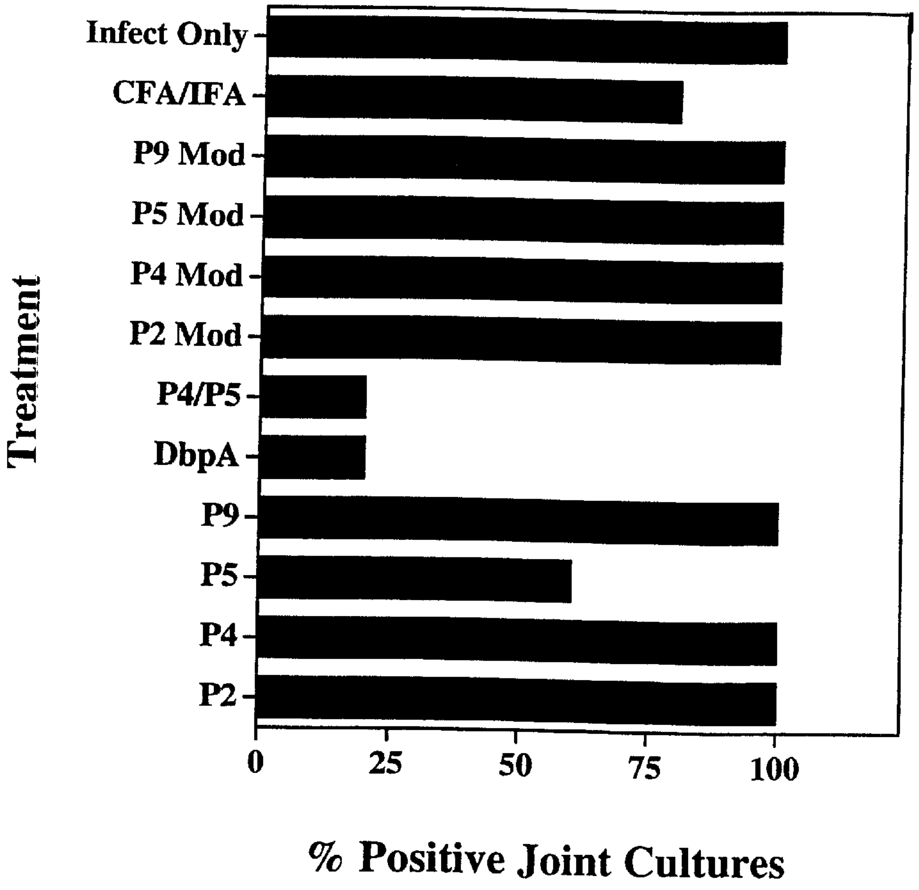
FIGURE 5-B

| | 14 | 32 | 40 | 50 | 51 | 82 | 91 | 102 | 104 | 163 | 170 |
|---|---|---|---|---|---|---|---|---|---|---|---|
| DbpA (297) | K | K | K | K | K | K | K | K | K | K | K |
| DbpA (Bb LP4) | K | K | K | K | K | K | K | K | K | K | K |
| DbpA (Bb SH2) | K | K | K | K | K | K | K | K | K | K | K |
| DbpA (Bb JDl) | K | K | K | K | K | K | K | K | K | K | K |
| DbpA (Bb B31) | K | K | K | K | K | K | K | ~K | K | K | K |
| DbpA (Bb G3940) | K | K | K | K | K | K | N | K | K | K | K |
| DbpA (Bb ZS7) | K | K | K | K | K | K | K | K | K | K | K |
| DbpA (Bb N40) | K | K | K | K | K | K | K | K | K | K | K |
| DbpA (Bb NCH-l) | K | K | K | K | K | K | K | K | K | K | K |
| DbpA (Bb 3028) | K | K | K | K | K | K | K | K | K | K | K |
| DbpA (Bb HBNC) | K | K | K | K | K | K | K | K | K | K | K |
| DbpA (Bb CA-3-87) | K | K | K | K | K | K | N | K | K | K | K |
| DbpA (Bb 25015) | K | K | K | K | K | K | K | K | K | K | K |
| DbpA (Bb ACA-l) | T | K | K | I | K | K | K | T | K | K | K |
| DbpA (3b HBl9) | K | K | K | K | K | K | K | K | K | K | K |
| DbpA (Ba B023) | T | K | K | I | K | K | E | T | K | K | K |
| DbpA (Ba PGau) | T | K | Q | R | A | K | K | K | K | K | K |
| DbpA (Bg IP90) | K | K | O | K | A | K | K | K | K | K | K |
| DbpA (Bb·JP7) | K | K | K | K | K | K | K | K | K | K | K |
| DbpA (Bb MCl) | K | K | K | K | K | K | K | K | K | K | K |
| DbpA (Bb IPF) | T | K | K | K | K | K | E | T | K | K | K |
| DbpA (Bb M7) | T | K | K | L | E | K | E | T | K | K | K |
| DbpA (Bb VS461) | T | K | K | I | K | K | E | T | K | K | K |
| DpbA (Bb VSPB) | K | K | Q | K | A | K | R | K | K | K | K |
| DpbA (Bb G25) | K | K | Q | K | A | K | R | K | K | K | K |
| DpbA (Bb PBr) | K | K | Q | K | A | K | R | K | K | K | K |
| DpbA (Bb 20047) | K | K | Q | K | A | K | K | K | K | K | K |
| DpbA (Bb JEM4) | K | K | Q | K | A | K | R | K | K | K | K |
| DpbA (Bb 153) | K | K | K | R | K | K | K | N | K | K | K |
| DpbA (Bb UOl) | K | K | Q | K | A | K | K | K | K | K | K |

FIGURE 7

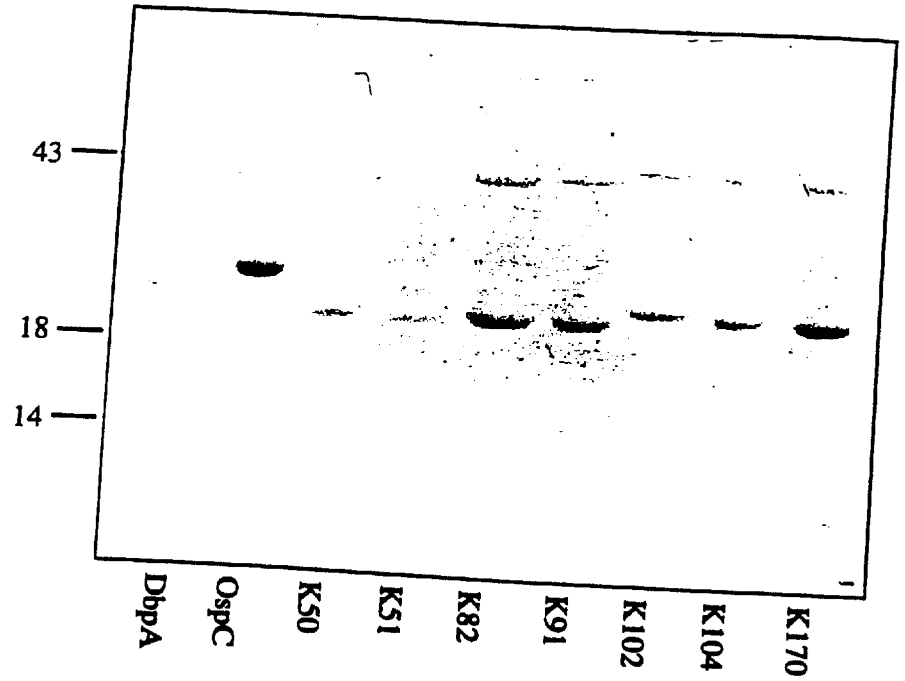
FIGURE 8-A

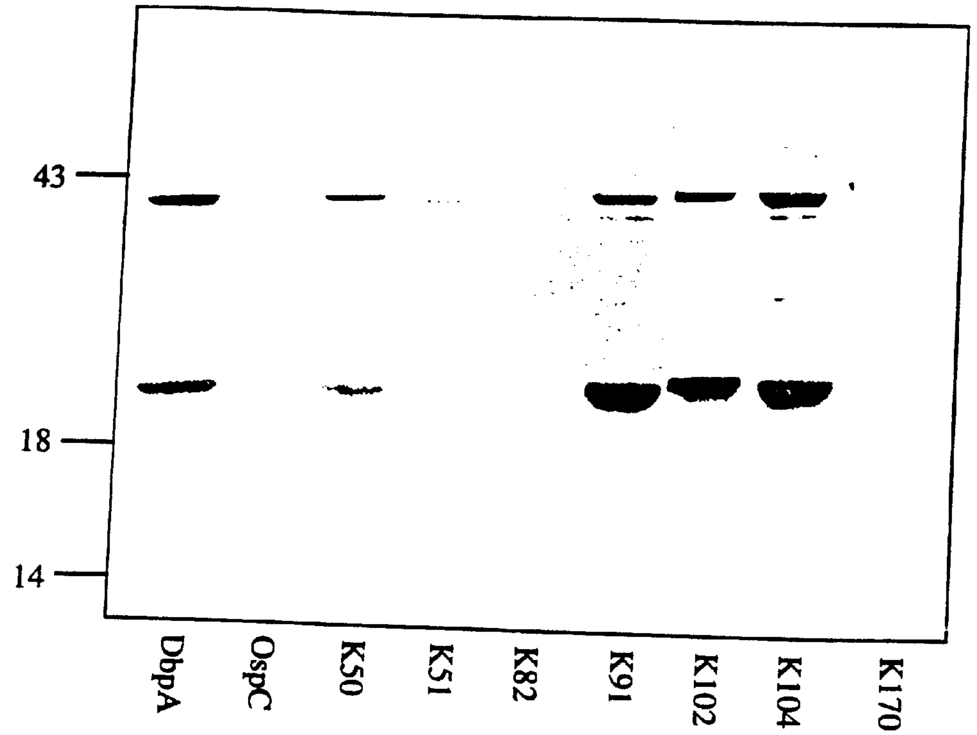
FIGURE 8-B

SEQUENCE LISTING

<160> NUMBER OF SEQ ID NOS: 36

<210> SEQ ID NO 1
<211> LENGTH: 187
<212> TYPE: PRT
<213> ORGANISM: Borrelia Burgdorferi -continued

```
<400> SEQUENCE: 1

Met Ile Lys Cys Asn Asn Lys Thr Phe Asn Asn Leu Leu Lys Leu Thr
1               5                   10                  15

Ile Leu Val Asn Leu Leu Ile Ser Cys Gly Leu Thr Gly Ala Thr Lys
            20                  25                  30

Ile Lys Leu Glu Ser Ser Ala Lys Ala Ile Val Asp Glu Ile Asp Ala
        35                  40                  45

Ile Lys Lys Lys Ala Ala Ser Met Gly Val Asn Phe Asp Ala Phe Lys
    50                  55                  60

Asp Lys Lys Thr Gly Ser Gly Val Ser Glu Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser
            180                 185


<210> SEQ ID NO 2
<211> LENGTH: 25
<212> TYPE: PRT
<213> ORGANISM: Artificial Sequence
<220> FEATURE:
<223> OTHER INFORMATION: Oligopeptide

<400> SEQUENCE: 2

Met Ile Lys Cys Asn Asn Lys Thr Phe Asn Asn Leu Leu Lys Leu Thr
1               5                   10                  15

Ile Leu Val Asn Leu Leu Ile Ser Cys
            20                  25


<210> SEQ ID NO 3
<211> LENGTH: 24
<212> TYPE: PRT
<213> ORGANISM: Artificial Sequence
<220> FEATURE:
<223> OTHER INFORMATION: Oligopeptide

<400> SEQUENCE: 3

Leu Leu Ile Ser Cys Gly Leu Thr Gly Ala Thr Lys Ile Lys Leu Glu
1               5                   10                  15

Ser Ser Ala Lys Ala Ile Val Asp
            20


<210> SEQ ID NO 4
<211> LENGTH: 25
<212> TYPE: PRT
<213> ORGANISM: Artificial Sequence
<220> FEATURE:
<223> OTHER INFORMATION: Oligopeptide

<400> SEQUENCE: 4
```

-continued

```
Ala Ile Val Asp Glu Ile Asp Ala Ile Lys Lys Lys Ala Ala Ser Met
1               5                   10                  15

Gly Val Asn Phe Asp Ala Phe Lys Asp
            20                  25


<210> SEQ ID NO 5
<211> LENGTH: 25
<212> TYPE: PRT
<213> ORGANISM: Artificial Sequence
<220> FEATURE:
<223> OTHER INFORMATION: Oligopeptide

<400> SEQUENCE: 5

Asp Ala Phe Lys Asp Lys Lys Thr Gly Ser Gly Val Ser Glu Asn Pro
1               5                   10                  15

Phe Ile Leu Glu Ala Lys Val Arg Ala
            20                  25


<210> SEQ ID NO 6
<211> LENGTH: 25
<212> TYPE: PRT
<213> ORGANISM: Artificial Sequence
<220> FEATURE:
<223> OTHER INFORMATION: Oligopeptide

<400> SEQUENCE: 6

Ala Lys Val Arg Ala Thr Thr Val Ala Glu Lys Phe Val Ile Ala Ile
1               5                   10                  15

Glu Glu Glu Ala Thr Lys Leu Lys Glu
            20                  25


<210> SEQ ID NO 7
<211> LENGTH: 25
<212> TYPE: PRT
<213> ORGANISM: Artificial Sequence
<220> FEATURE:
<223> OTHER INFORMATION: Oligopeptide

<400> SEQUENCE: 7

Thr Lys Leu Lys Glu Thr Gly Ser Ser Gly Glu Phe Ser Ala Met Tyr
1               5                   10                  15

Asp Leu Met Phe Glu Val Ser Lys Pro
            20                  25


<210> SEQ ID NO 8
<211> LENGTH: 25
<212> TYPE: PRT
<213> ORGANISM: Artificial Sequence
<220> FEATURE:
<223> OTHER INFORMATION: Oligopeptide

<400> SEQUENCE: 8

Glu Val Ser Lys Pro Leu Gln Glu Leu Gly Ile Gln Glu Met Thr Lys
1               5                   10                  15

Thr Val Ser Met Ala Ala Glu Glu Asn
            20                  25


<210> SEQ ID NO 9
<211> LENGTH: 25
<212> TYPE: PRT
<213> ORGANISM: Artificial Sequence
<220> FEATURE:
<223> OTHER INFORMATION: Oligopeptide
```

-continued

<400> SEQUENCE: 9

```
Ala Ala Glu Glu Asn Pro Pro Thr Thr Ala Gln Gly Val Leu Glu Ile
1               5                   10                  15

Ala Lys Lys Met Arg Glu Lys Leu Gln
            20                  25
```

<210> SEQ ID NO 10
<211> LENGTH: 27
<212> TYPE: PRT
<213> ORGANISM: Artificial Sequence
<220> FEATURE:
<223> OTHER INFORMATION: Oligopeptide

<400> SEQUENCE: 10

```
Arg Glu Lys Leu Gln Arg Val His Lys Lys Asn Gln Asp Thr Leu Lys
1               5                   10                  15

Lys Lys Asn Thr Glu Asp Ser Thr Ala Lys Ser
            20                  25
```

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide

<400> SEQUENCE: 11
cgcggatcca acaatttact taaacta 27

<210> SEQ ID NO 12
<211> LENGTH: 26
<212> TYPE: DNA
<213> ORGANISM: Artificial Sequence
<220> FEATURE:
<223> OTHER INFORMATION: Oligonucleotide

<400> SEQUENCE: 12
gcgctgcagt tacgattagc agtgct 26

<210> SEQ ID NO 13
<211> LENGTH: 39
<212> TYPE: DNA
<213> ORGANISM: Artificial Sequence
<220> FEATURE:
<223> OTHER INFORMATION: Oligonucleotide

<400> SEQUENCE: 13
cgcggatcca acttttaaca atttacttgc actaactat 39

<210> SEQ ID NO 14
<211> LENGTH: 40
<212> TYPE: DNA
<213> ORGANISM: Artificial Sequence
<220> FEATURE:
<223> OTHER INFORMATION: Oligonucleotide

<400> SEQUENCE: 14
aacaggagca acagcaatca aattagaatc atcagctaaa 40

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide -continued

<400> SEQUENCE: 15
tttagctgat gattctaatt tgattgctgt tgctcctgtt 40

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide

<400> SEQUENCE: 16
aattagaatc atcagctagc gccattgtag 30

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide

<400> SEQUENCE: 17
ctacaatggc gctagctgat gattctaatt 30

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide

<400> SEQUENCE: 18
agatgcaatt gcaaaaaagg ctgct 25

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide

<400> SEQUENCE: 19
agcagccttt tttgcaattg catct 25

<210> SEQ ID NO 20
<211> LENGTH: 26
<212> TYPE: DNA
<213> ORGANISM: Artificial Sequence
<220> FEATURE:
<223> OTHER INFORMATION: Oligonucleotide

<400> SEQUENCE: 20
agatgcaatt gcagcagcgg ctgctt 26

<210> SEQ ID NO 21
<211> LENGTH: 26
<212> TYPE: DNA
<213> ORGANISM: Artificial Sequence
<220> FEATURE:
<223> OTHER INFORMATION: Oligonucleotide

<400> SEQUENCE: 21
aagcagccgc tgctgcaatt gcatct 26

<210> SEQ ID NO 22

-continued

<211> LENGTH: 26
<212> TYPE: DNA
<213> ORGANISM: Artificial Sequence
<220> FEATURE:
<223> OTHER INFORMATION: Oligonucleotide

<400> SEQUENCE: 22
agatgcaatt gcagcagcgg ctgctt 26

<210> SEQ ID NO 23
<211> LENGTH: 26
<212> TYPE: DNA
<213> ORGANISM: Artificial Sequence
<220> FEATURE:
<223> OTHER INFORMATION: Oligonucleotide

<400> SEQUENCE: 23
aagcagccgc tgctgcaatt gcatct 26

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide

<400> SEQUENCE: 24
atacttgaag cagcagtgcg agct 24

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide

<400> SEQUENCE: 25
agtagctcgc actgctgctt caag 24

<210> SEQ ID NO 26
<211> LENGTH: 18
<212> TYPE: DNA
<213> ORGANISM: Artificial Sequence
<220> FEATURE:
<223> OTHER INFORMATION: Oligonucleotide

<400> SEQUENCE: 26
tagcggaagc attcgtaa 18

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide

<400> SEQUENCE: 27
ttacgaatcc ttccgcaa 18

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide

<400> SEQUENCE: 28

-continued aagctactgc acttaaagaa actgg 25

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide

<400> SEQUENCE: 29
ccagtttctt taagtgcagt agct 24

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide

<400> SEQUENCE: 30
aagctactaa acttgcagaa actgg 25

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide

<400> SEQUENCE: 31
ccagtttctg caagtttagt agctt 25

<210> SEQ ID NO 32
<211> LENGTH: 26
<212> TYPE: DNA
<213> ORGANISM: Artificial Sequence
<220> FEATURE:
<223> OTHER INFORMATION: Oligonucleotide

<400> SEQUENCE: 32
aaaatgagag aagcattaca aagggt 26

<210> SEQ ID NO 33
<211> LENGTH: 26
<212> TYPE: DNA
<213> ORGANISM: Artificial Sequence
<220> FEATURE:
<223> OTHER INFORMATION: Oligonucleotide

<400> SEQUENCE: 33
accctttgta atgcttctct catttt 26

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide

<400> SEQUENCE: 34
ttcacaaggc aaaccaagac a 21

<210> SEQ ID NO 35
<211> LENGTH: 21
<212> TYPE: DNA

-continued

```
<213> ORGANISM: Artificial Sequence
<220> FEATURE:
<223> OTHER INFORMATION: Oligonucleotide

<400> SEQUENCE: 35

tgtcttggtt tgccttgtga a                                        21


<210> SEQ ID NO 36
<211> LENGTH: 19
<212> TYPE: PRT
<213> ORGANISM: Artificial Sequence
<220> FEATURE:
<223> OTHER INFORMATION: Oligopeptide
<220> FEATURE:
<221> NAME/KEY: MISC_FEATURE
<222> LOCATION: (1)..(1)
<223> OTHER INFORMATION: X = Ornithine

<400> SEQUENCE: 36

Xaa Ser Lys Ile Thr Val Asp Asn Thr Lys Asn Thr Ile Asp Val Thr
1               5                   10                  15

Ile Gln Gly
```

DECORIN BINDING PROTEIN ESSENTIAL PEPTIDES AND METHODS OF USE

BACKGROUND OF THE INVENTION

1. Field of the Invention

The present invention relates generally to the fields of molecular biology and microbiology. More particularly, it concerns a method of use of residues necessary for ligand binding in a decorin binding protein, DbpA. More particularly, certain embodiments concern methods and compositions comprising DNA segments, and peptides derived from bacterial species.

2. Description of Related Art

Lyme disease (LD) is a chronic, multisystemic disease caused by the spirochete *Borrelia burgdorferi* (1). It is transmitted to humans and other mammals during the blood meal of Ixodes ticks (2, 3) and it is the most common vector-borne disease in the United States (1). This initial skin infection is often accompanied by a local rash (erythema migrans) which can be followed by a general flu-like illness. Untreated Lyme borreliosis can develop into a chronic, multisystemic disorder that may affect the joints (Lyme arthritis), skin, heart, and central nervous system (1).

Microbial adhesion to and colonization of host tissue is an early, critical event in an infection process. In the case of LD, host tissue adherence appears to be of importance during different stages of the disease process. Initially, during an infected tick's blood meal, a small number of spirochetes are deposited in the dermis of the host where the bacteria appear to colonize collagen fibers (32,33). As the infection disseminates to other tissues, bacteria may colonize additional extracellular matrix (ECM) structures and host cells may be involved. Adherence of *Borrelia burgdorferi* to collagen fibers involves a specific binding of the spirochete to decorin, a dermatan sulfate proteoglycan which is associated with and "decorates" collagen fibers (17, 18). A dermal route of entry into the host appears to be important for the development of disease. Spirochetes administered intravenously are rapidly and effectively cleared by Kupffer cells in the liver (34), whereas those inoculated intradermaly consistently establish infection (35). Perhaps the initial dermal colonization allows the organism to adapt to in vivo conditions before blood stream dissemination.

The genes coding for the two decorin-binding proteins (DbpA and DbpB) which are expressed at the surface of the spirochete as lipoproteins and act as adhesins of the MSCRAMM (Microbial Surface Component Recognizing Adhesive Matrix Molecule) family have been cloned and sequenced. Recombinant forms of DbpA and DbpB are capable of binding to decorin and DbpA effectively inhibits the adherence of *Borrelia burgdorferi* to a decorin substrate (17).

Active and passive immunization of mice using DbpA and DbpA antiserum, respectively, protected against challenge with *B. burgdofferi* (10,11). DbpA sequences vary significantly among different Borrelia strains. Nevertheless, antibodies to one recombinant form of DbpA can confer broad protection against various strains, suggesting that at least some immunoprotective epitopes are conserved.

During transmission from the tick's midgut to the vertebrate host, Borrelia spirochetes undergo antigenic modulations, which includes the up- and down-regulation of various surface-exposed proteins (e.g. OspA, B. and C) (4, 5). OspA has been the most widely studied Borrelia protein, and vaccine trials in both murine models of LD and in humans indicate that this protein can confer protection to infection against the Lyme spirochete (6–8).

However, some drawbacks in OspA-derived vaccine formulations exist. Since OspA expression occurs primarily in the tick vector, high anti-OspA titers need to be maintained to inhibit spirochete transmission (9–11) and anti-OspA antibodies lose efficacy against host-adapted Borrelia (12). Furthermore, protection against heterologous Borrelia strains is poor to nonexistent (13–16). Additionally, modulation of OspA expression by *B. burgdorferi* may limit the efficacy of anti-OspA antibodies to spirochetes residing in the midgut, and cross-reactivity of OspA with human lymphocyte function-associated antigen-1 (hLFA-1) may be a critical factor in treatment-resistant Lyme arthritis (5, 9, 10, 24).

The decorin binding proteins (DbpA and DbpB) of *Borrelia burgdorferi* are adhesins of the MSCRAMM family (17) which recognize the proteoglycan decorin and may play a role in the colonization of the skin and establishment of disease (17, 18). Unlike OspA, DbpA expression on *B. burgdorferi* is expressed in the vertebrate host (19). Recent work testing DbpA as a vaccine candidate against heterologous Borrelia strains demonstrated that DbpA-based formulations are capable of conferring protection against challenge with *B. burgdorferi* (19), and may be more effective than OspA formulations. (11).

Applicants' discovery of antigenic determinants on proteins capable of eliciting protective immunity are used to design novel peptides that may have the potential of mimicking the protective effects of native proteins. The risk of cross-reactivity against the host is reduced since peptide vaccines are chemically defined structures. Furthermore, peptides are stable and no infectious materials are used in their production (25).

SUMMARY OF THE INVENTION

Accordingly, the present invention provides several novel methods and related biological compositions for protecting against infection with *Borrelia burgdorferi.* Also provided are methods of identifying substances that alter or modulate the interaction of various decorin binding proteins with decorin, and the substances so identified.

The invention first provides a protein fragment or related peptide that spans the critical binding regions required for DbpA/decorin adhesion.

The invention also provides a method of inhibiting the binding of *B. burgdorferi* to decorin by contacting the decorin with a protein fragment or related peptide that spans the critical binding regions required for DbpA/decorin adhesion and thus preventing infection with *B. burgdorferi.*

It is a further aspect of the present invention to provide isolated DbpA-derived peptide fragments or related peptides that are able to inhibit adhesion to the immobilized extracellular matrix of host cells or the surface of implanted biomaterials.

It is a further object of the present invention to provide a vaccine which can be used in generating an immonogenic reaction in a host and which thus can be used in treating or preventing infection by bacteria such as *B. burgdorferi.*

It is still further an object of the present invention to generate antisera and antibodies to the decorin binding proteins from *B. burgdorferi bacteria* which can also be useful in methods of treatment which can inhibit binding of the *B. burgdorferi* bacteria to host cells or to implanted biomaterials and thus be employed in order to treat or prevent *B. burgdorferi* infections.

It is a further object of the present invention to provide improved materials and methods for detecting and differentiating decorin-binding proteins in *B. burgdorferi* in clinical and laboratory settings.

These and other objects are provided by virtue of the present invention which comprises a method of using an isolated decorin binding protein identified as the DbpA protein from *B. burgdorferi,* which has been determined to bind to decorin, along with the sequences governing the specific decorin-binding domains of this proteins. The isolated *B. burgdorferi* proteins of the present invention, or active portions or fragments thereof can thus be utilized in methods of treating or preventing *B. burgdorferi* infection through the inhibition of the ability of the bacteria to bind to decorin, or through the development of antibodies thereto which will prevent or inhibit the bacteria's ability to bind to host cells.

In another aspect of the present invention, there is also provided antisera and antibodies generated against the decorin binding proteins of the present invention which also can be utilized in methods of treatment which involve inhibition of the attachment of the DbpA proteins to decorin.

Accordingly, in accordance with the invention, antisera and antibodies raised against the DbpA proteins, or immunogenic portions thereof, may be employed in vaccines, and other pharmaceutical compositions containing the proteins for therapeutic purposes are also provided herein. In addition, diagnostic kits containing the appropriate proteins, or antibodies or antisera raised against them, are also provided so as to detect bacteria expressing these proteins.

In certain aspects of the invention, the protein fragment or related peptide composition is dispersed in a pharmaceutically-acceptable carrier. In other aspects of the invention, the decorin to be contacted is comprised within an animal, and the protein fragment composition is administered to the animal. In a particular aspect of the invention, the animal is a human subject.

The invention also provides a method of inhibiting decorin binding protein from binding decorin in a blood sample, the method comprising contacting the blood sample with an amount of a the DbpA-derived peptide fragment or related peptide composition effective to inhibit decorin/DbpA binding in the sample.

In another embodiment of the invention, the DbpA-derived peptide fragment or related peptide composition is dispersed in a pharmaceutically-acceptable carrier. In an additional aspect of the invention, the blood sample containing decorin is found within an animal, and the protein, fragment or related peptide composition is administered to the animal. In a further aspect of the invention, the animal is a human subject.

Suitable methods of administration of any pharmaceutical composition disclosed in this application include, but are not limited to, topical, oral, anal, vaginal, intravenous, intraperitoneal, intramuscular, subcutaneous, intranasal and intradermal administration.

The preferred dose for human administration will be determined based on the needs of the individual patient and the nature of the disorder being treated. Based on a preferred dose range, equivalent dosages for heavier body weights can be determined. The dose should be adjusted to suit the individual to whom the composition is administered and will vary with age, weight and metabolism of the individual. The vaccine may additionally contain stabilizers or pharmaceutically acceptable preservatives, such as thimerosal (ethyl (2-mercaptobenzoate-S)mercury sodium salt) (Sigma Chemical Company, St. Louis, Mo.).

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

The invention additionally provides a method of preventing Lyme disease in an animal, comprising providing to an animal an amount of a DbpA-derived peptide fragment or related peptide pharmaceutical composition effective to inhibit the binding of DbpA to decorin in the animal. In certain aspects, the invention provides a method of inhibiting the binding of DbpA to decorin in an animal, comprising providing to an animal an amount of a decorin binding DbpA-derived protein fragment or related peptide pharmaceutical composition effective to bind to decorin in the animal.

Also provided is a method for identifying a candidate substance that alters the binding of a DbpA-derived protein fragment or related peptide to decorin, that may be characterized as comprising the steps of admixing a composition comprising a DbpA-derived protein fragment or related peptide with a decorin preparation and a candidate substance, and determining the ability of the DbpA-derived protein fragment or related peptide to bind to the decorin preparation in the presence and in the absence of the candidate substance, wherein the ability of the candidate substance to alter the binding of the DbpA-derived protein fragment or related peptide to the decorin preparation is indicative of a candidate substance that alters the binding of a DbpA-derived protein or peptide fragment to decorin. In a further aspect of the invention, the DbpA-derived protein or peptide fragment is prepared by recombinant means.

In a particular embodiment of the invention, the method is further defined as a method for identifying a candidate substance that promotes the binding of a DbpA-derived protein fragment or related peptide to decorin, comprising determining the ability of a candidate substance to increase the binding of a DbpA-derived protein fragment or related peptide to decorin upon admixing with a composition that comprises a DbpA-derived protein fragment or related peptide. In another aspect of the invention, the method is further defined as a method for identifying a candidate substance that inhibits the binding of a DbpA-derived protein fragment or related peptide to decorin, comprising determining the ability of a candidate substance to decrease the binding of a DbpA-derived protein fragment or related peptide to decorin upon admixing with a composition that comprises a DbpA-derived protein fragment or related peptide and a decorin preparation.

Further provided is a modulator of DbpA-derived protein or peptide fragment binding to decorin, prepared by a process comprising the steps of admixing a composition comprising a DbpA-derived protein or peptide fragment with a decorin preparation and a candidate modulator, identifying a modulator that alters the binding of the DbpA-derived protein or peptide fragment to decorin by determining the ability of the DbpA-derived protein or peptide to bind to the decorin preparation in the presence and in the absence of the candidate modulator, wherein the ability of the candidate modulator to alter the binding of the DbpA-derived protein or peptide fragment to the decorin preparation is indicative of a candidate modulator that alters the binding of a DbpA-derived protein or peptide fragment to decorin, and obtaining the modulator so identified.

Thus, the invention also provides a method of modulating DbpA-derived protein or peptide fragment binding to decorin, comprising contacting a composition comprising decorin and a DbpA-derived protein or DbpA-derived peptide fragment with an effective amount of a substance that modulates DbpA-derived protein or peptide fragment binding to decorin. In one aspect of the invention, the method may be further defined as a method for promoting the binding of a DbpA-derived protein or peptide fragment to decorin, comprising contacting the composition with an effective amount of a substance that increases the binding of a DbpA-derived protein or peptide fragment to decorin. In another aspect of the invention, the method may be further defined as a method for inhibiting the binding of a DbpA-derived protein or peptide fragment to decorin, comprising contacting the composition with an effective amount of a substance that decreases the binding of a DbpA-derived protein or peptide fragment to decorin.

In a particular embodiment of the invention, the composition is comprised within an animal. In an additional embodiment of the invention, the animal is a human subject.

The invention also provides a method for identifying a candidate DbpA-derived peptide fragment with improved decorin binding, that may be characterized as comprising the steps of admixing a composition comprising a candidate DbpA-derived peptide fragment with a decorin preparation, and determining the ability of the candidate DbpA-derived peptide fragment to bind to the decorin preparation, wherein a candidate DbpA-derived peptide fragment that exhibits improved binding to decorin as compared to wild-type DbpA is indicative of a candidate DbpA-derived peptide fragment with improved decorin binding.

DETAILED DESCRIPTION OF THE INVENTION

Applicants provide that at least two peptides, P4 (SEQ ID 5) and P5 (SEQ ID 6), have the ability of eliciting both DTH to DbpA and a protective immune response to Borrelia infection. Combinations of these peptides as well as multimeric formulations have similar potential in human use.

Accordingly, the DbpA-derived protein or peptide fragments used in the present invention may be utilized in many applications for the treatment, identification, or prevention of Borrelia infections. For example, compositions containing isolated DbpA-derived protein or peptide fragments, specifically the fragments or portions containing the decorin-binding domain, may be used as blocking agents to bind to decorin-binding sites in a patient, or in implanted biomaterials or other instruments used in surgical operations, and thus be able to inhibit the binding of Borrelia bacteria to decorin and thereby treat or prevent Borrelia infection. In addition, as described more fully below, the DbpA-derived protein or peptide fragments of the invention, including active portions and domains thereof, may be utilized to generate antibodies which can treat or prevent Borrelia infection, either when generated directly in the patient through the use of vaccines, or through therapeutic compositions containing antibodies to the DbpA-derived protein or its active portions or fragments.

In accordance with the present invention, a method of inhibiting the attachment of Borrelia bacteria to decorin is provided which comprises administering an DbpA-derived protein or peptide fragment, in an amount sufficient to inhibit the attachment of Borrelia bacteria to decorin, and such administration may be utilized to block the sites for Borrelia attachment in a patient, a medical device, or a bioimplant. A method is also provided for treating or preventing Borrelia infection in a patient comprising administering an DbpA-derived protein or peptide fragment, such as in a pharmaceutical composition, in an amount sufficient to treat or prevent an Borrelia infection. As would be recognized by one skilled in this art, the precise treatment regimen will be dependent upon the circumstances surrounding the need for treatment, including, e.g., the nature and condition of the patient, the extent and the seriousness of the afflicted area, and the amenability of the patient to particular forms of treatment. Similarly, where the method involves other objects such as biomedical instruments or implants made from biological materials, an appropriate amount and treatment form will be determined based on the circumstances and the materials involved.

According to one aspect of the present invention, the isolated decorin-binding DbpA-derived protein or peptide fragments of the present invention may be used in combination with other peptides. In a particular embodiment of the present invention, the isolated decorin-binding DbpA-derived protein or peptide fragments of the present invention are used in combination with adhesins.

As would be recognized by one skilled in the art, the isolated decorin-binding DbpA-derived protein or peptide fragments of the present invention may be obtained through conventional isolation or recombination methods well known in the art. For example, in a conventional recombinant procedure, a cloning vector, such as a plasmid or phage DNA is cleaved with a restriction enzyme, and the DNA sequence encoding the DbpA-derived protein or peptide fragment, or its binding or other active fragments thereof, such as consensus or variable sequence amino acid motifs, is inserted into the cleavage site and ligated. The cloning vector is then inserted into a host to produce the protein or fragment. Suitable hosts include bacterial hosts such as *Escherichia coli, Bacillus subtilis,* yeasts and other cell cultures. Production and purification of the gene product may be achieved and enhanced using known molecular biology techniques.

In accordance with the present invention, pharmaceutical compositions are also provided which contain the DbpA-derived protein or peptide fragments, or active portions as described herein, and which may be formulated in combination with a suitable pharmaceutical vehicle, excipient or carrier well know in the art. Examples of some suitable vehicles, carriers and excipients would include saline, dextrose, water, glycerol, ethanol, other therapeutic compounds, and combinations thereof. The formulation should be appropriate for the mode of administration. The DbpA-derived protein or peptide fragment compositions of the present invention will thus be useful for interfering with, modulating, or inhibiting binding interactions between Borrelia bacteria and decorin on host cells.

In addition to the structures of the DbpA-derived protein or peptide fragments as described herein, as would be recognized by one of ordinary skill in this art, modification and changes may be made in the structure of the proteins and peptides of the present invention and DNA segments which encode them and still obtain a functional molecule that encodes a protein or peptide with desirable characteristics. The amino acid changes may be achieved by changing the codons of the DNA sequence. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In addition, amino acid substitutions are also possible without affecting the decorin binding ability of the isolated proteins of the invention, provided that the substitutions provide amino acids having sufficiently similar properties to the ones in the original sequences.

Accordingly, acceptable amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The isolated proteins of the present invention can be prepared in a number of suitable ways known in the art including typical chemical synthesis processes to prepare a sequence of polypeptides.

The synthetic polypeptides of the invention can thus be prepared using the well known techniques of solid phase, liquid phase, or peptide condensation techniques, or any combination thereof, can include natural and unnatural amino acids. Amino acids used for peptide synthesis may be standard Boc ($N^a$-amino protected $N^a$-t-butyloxycarbonyl) amino acid resin with the standard deprotecting, neutralization, coupling and wash protocols of the original solid phase procedure of Merrifield, or the base-labile $N^a$-amino protected 9-fluorenylmethoxycarbonyl (Fmoc) amino acids first described by Carpino and Han. Both Fmoc and Boc $N^a$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^a$-protecting groups that are familiar to those skilled in this art. Solid phase peptide synthesis may be accomplished by techniques familiar to those in the art and provided, for example, in Stewart and Young, 1984, *Solid Phase Synthesis,* Second Edition, Pierce Chemical Co., Rockford, Ill.; Fields and Noble, 1990, *lnt. J. Pept Protein Res.* 35:161–214, or using automated synthesizers, such as sold by ABS. Thus, polypeptides of the invention may comprise D-amino acids, a combination of D- and L-amino acids, and various "designer" amino acids (e.g. β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. additionally, by assigning specific amino acids at specific coupling steps, α-helices, β turns, β sheets, γ-turns, and cyclic peptides can be generated.

In a further embodiment, subunits of peptides that confer useful chemical and structural properties may be used in accordance with the invention. For example, peptides comprising D-amino acids will be resistant to L-amino acid-specific proteases in vivo. In addition, the present invention envisions preparing peptides that have more well defined structural properties, and the use of peptidomimetics and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown or protease activity. It is also well known that in certain systems, constrained peptides show enhanced functional activity (Hruby, *Life Sciences,* 31:189–199, 1982); (Hruby et al., *Biochem J.,* 268:249–262, 1990).

In another aspect of the present invention, the isolated natural, recombinant or synthetic proteins of the present invention, or antigenic portions thereof (including epitope-bearing fragments), or fusion proteins including the DbpA-derived protein or peptide fragments as described above, can be administered to animals as immunogens or antigens, alone or in combination with an adjuvant, for the production of antibodies reactive with the DbpA-derived protein or peptide fragments or active portions thereof. Accordingly, the DbpA-derived protein or peptide fragments of the present invention, or active domains thereof, may be useful as vaccines to generate an immune response in a patient, or in methods of generating antibodies in a host organism which can then be introduced into a patient in order to prevent or treat an Borrelia infection. In addition, the DbpA-derived protein or peptide fragments can be used to screen antibodies or antisera for hyperimmune patients from whom can be derived specific antibodies having a very high affinity for the proteins.

Antibodies to DbpA, or its binding domain, can also be used in accordance with the invention for the specific detection of decorin-binding Borrelia proteins, for the prevention of infection from the Borrelia, for the treatment of an ongoing infection, or for use as research tools. The term "antibodies" as used herein includes monoclonal, polyclonal, chimeric, single chain, bispecific, simianized, and humanized or primatized antibodies as well as Fab fragments, including the products of an Fab immunoglobulin expression library. Generation of any of these types of antibodies or antibody fragments is well known to those skilled in the art.

In addition to their use in treatment or prevention of Lyme disease, any of the above described antibodies may be labeled directly with a detectable label for identification and quantification of Borrelia. Labels for use in immunoassays are generally known to those skilled in the art and include enzymes, radioisotopes, and fluorescent, luminescent, diaminobenzene and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to the decorin-binding DbpA-derived protein or peptide fragments of the present invention, or active portions or fragments thereof, such as the binding domain, may also be used in production facilities or laboratories to isolate additional quantities of the proteins, such as by affinity chromatography. For example, antibodies to the decorin-binding protein DbpA-derived protein or peptide fragment or its binding domain may also be used to isolate additional amounts of decorin.

The isolated DbpA-derived protein or peptide fragments of the present invention, or active fragments thereof, and antibodies to the proteins, may thus be utilized in many applications involving the treatment, prevention and diagnosis of Borrelia bacterial infections as described above, or for the development of anti-Borrelia vaccines for active or passive immunization. Further, when administered as pharmaceutical composition to a patient or used to coat medical devices or polymeric biomaterials in vitro and in vivo, both the proteins and the antibodies are useful as blocking agents to prevent or inhibit the binding of Borrelia to decorin at the wound site or the biomaterials themselves. Preferably, the antibody is modified so that it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522–525 (1986) or Tempest et al. *Biotechnology* 9:266–273 (1991).

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureterallurinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the protein, antibody, or active fragment to a surface of the device, preferably an outer surface that would be exposed to Borrelia bacterial infection. The surface of the device need not be entirely covered by the protein, antibody or active fragment.

In addition, the present invention may be utilized as immunological compositions, including vaccines, and other pharmaceutical compositions containing the DbpA-derived protein or peptide fragment or its active regions, are included within the scope of the present invention. Either the DbpA-derived protein or peptide fragment, or its decorin-binding domain, or other active or antigenic fragments thereof, or fusion proteins thereof, can be formulated and packaged, alone or in combination with other antigens, using methods and materials known to those skilled in the art for vaccines. The immunological response may be used therapeutically or prophylactically and may provide antibody immunity or cellular immunity, such as that produced by T lymphocytes.

The immunological compositions, such as vaccines, and other pharmaceutical compositions can be used alone or in combination with other blocking agents to protect against human and animal infections caused by or exacerbated by Borrelia bacteria.

To enhance immunogenicity, the proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 Daltons, preferably greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The isolated DbpA-derived protein or peptide fragment, may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) may also be useful.

The term "vaccine" as used herein includes DNA vaccines in which the nucleic acid molecule encoding for a decorin-binding DbpA-derived protein or peptide fragment is used in a pharmaceutical composition is administered to a patient. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), coprecipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992 and Eisenbraun et al., *DNA Cell Biol.* 12:791, 1993), and in vivo infection using cloned retroviral vectors (Seeger et al., *Proc. Natl. Acad. Sci.* 81:5849, 1984).

In another embodiment, the invention is a method of using a polynucleotide which comprises contiguous nucleic acid sequences capable of being expressed to produce an DbpA gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to ensure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a $CD8^+$ response to NP that protected mice against challenge with heterologous strains of flu. (See Montgomery, D. L. et al., *Cell Mol Biol,* 43(3):285–92, 1997 and Ulmer, J. et al., *Vaccine,* 15(8):792–794, 1997.)

Cell-mediated immunity is important in controlling infection. Since DNA immunization can evoke both humoral and cell-mediated immune responses, its greatest advantage may be that it provides a relatively simple method to survey a large number of *B. burgdorferi* genes for their vaccine potential.

The amount of expressible DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, effective dose ranges of roughly about 1 ng to 5 mg, 100 ng to 2.5 mg, 1 μg to 750 μg, and preferably about 10 μg to 300 μg, of DNA may be suitable, e.g., if administered directly into muscle tissue. Subcutaneous injection, intradermal introduction, impression through the skin, and other modes of administration such as intraperitoneal, intravenous, or inhalation delivery may also be suitable as would be recognized by one skilled in this art. It is also contemplated that booster vaccinations may be provided. Following vaccination with a polynucleotide immunogen, boosting with protein immunogens such as the isolated ACE protein or the isolated A domain is also contemplated.

The polynucleotide may be "naked", that is, unassociated with any proteins, adjuvants or other agents which affect the recipient's immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

It is recognized by those skilled in the art that an optimal dosing schedule for a vaccination regimen as set forth above will vary according to the needs of the particular patient, but may include as many as one to six or more administrations of the immunizing entity given at intervals of as few as two to four weeks, to as long as five to ten years, or occasionally at even longer intervals, as needed.

Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

In a preferred embodiment, a vaccine is packaged in a single dosage for immunization by parenteral (i.e., intramuscular, intradermal or subcutaneous) administration or nasopharyngeal (i.e., intranasal) administration. If intramuscularly introduced, the vaccine is preferably injected directly intramuscularly into the deltoid muscle. The vaccine is preferably combined with a pharmaceutically acceptable carrier to facilitate administration. The carrier is usually water or a buffered saline, with or without a preservative. The vaccine may be lyophilized for resuspension at the time of administration or in solution.

Microencapsulation of the protein will give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, polyamides, poly (D,L-lactide-co-glycolide) (PLGA) and other biodegradable polymers. The use of PLGA for the controlled release of antigen is reviewed by Eldridge et al., Current Topics in Microbiology and Immunology, 146:59–66 (1989).

The preferred dose for human administration will be determined based on the needs of the individual patient and the nature of the disorder being treated, for example ranging 0.01 mg/kg to 10 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers or pharmaceutically acceptable preservatives, such as thimerosal (ethyl(2-mercaptobenzoate-S)mercury sodium salt) (Sigma Chemical Company, St. Louis, Mo.).

When labeled with a detectable biomolecule or chemical, the DbpA-derived protein or peptide fragment described herein is useful for purposes such in vitro detection of decorin in a sample. Laboratory research may also be facilitated through use of such protein-label conjugates. Various types of labels and methods of conjugating the labels to the proteins are well known to those skilled in the art. Several specific labels are set forth below. The labels are particularly useful when conjugated to a protein such as an antibody or receptor. For example, the protein can be conjugated to a radiolabel such as, but not restricted to, $^{32}P$, $^{3}H$, $^{14}C$, $^{35}S$, $^{125}I$, or 131I. Detection of a label can be by methods such as scintillation counting, gamma ray spectrometry or autoradiography.

Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allophycocyanin, phycocyanin, rhodamine, and Texas Red. The fluorogens are generally detected by a fluorescence detector.

The DbpA-derived protein can alternatively be labeled with a chromogen to provide an enzyme or affinity label. For example, the protein can be biotinylated so that it can be utilized in a biotin-avidin reaction, which may also be coupled to a label such as an enzyme or fluorogen. For example, the protein can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol[a]) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, proteins may be labeled with colloidal gold for use in immunoelectron microscopy in accordance with methods well known to those skilled in the art.

The location of a ligand in cells can be determined by labeling an antibody as described above and detecting the label in accordance with methods well known to those skilled in the art, such as immunofluorescence microscopy using procedures such as those described by Warren and Nelson (*Mol. Cell. Biol.,* 7: 1326–1337, 1987).

In addition to the therapeutic compositions and methods described above, the DbpA-derived protein or peptide fragments, nucleic acid molecules or antibodies may also be useful for interfering with the initial physical interaction between a pathogen and mammalian host responsible for infection, such as the adhesion of bacteria, to mammalian extracellular matrix proteins such as decorin on in-dwelling devices or to extracellular matrix proteins in wounds; to block DbpA-mediated mammalian cell invasion; to block bacterial adhesion between decorin and bacterial DbpA proteins or portions thereof that mediate tissue damage; and, to block the normal progression of pathogenesis in infections initiated other than by the implantation of in-dwelling devices or surgical techniques.

The DbpA-derived protein or peptide fragments, are useful in a method for screening compounds to identify compounds that inhibit decorin binding of Borrelia to host molecules. In accordance with the method, the compound of interest is combined with one or more of the DbpA-derived protein or peptide fragments and the degree of binding of the protein to decorin or other extracellular matrix proteins is measured or observed. If the presence of the compound results in the inhibition of protein-decorin binding, for example, then the compound may be useful for inhibiting Borrelia in vivo or in vitro. The method could similarly be used to identify compounds that promote interactions of Borrelia with host molecules. The method is particularly useful for identifying compounds having bacteriostatic or bacteriocidal properties.

For example, to screen for Borrelia agonists or antagonists, a synthetic reaction mixture, a cellular compartment (such as a membrane, cell envelope or cell wall) containing one or more of the DbpA-derived protein or peptide fragments and a labeled substrate or ligand of the protein is incubated in the absence or the presence of a compound under investigation. The ability of the compound to agonize or antagonize the protein is shown by a decrease in the binding of the labeled ligand or decreased production of substrate product. Compounds that bind well and increase the rate of product formation from substrate are agonists. Detection of the rate or level of production of product from substrate may be enhanced by use of a reporter system, such as a colorimetric labeled substrate converted to product, a reporter gene that is responsive to changes in ACE nucleic acid or protein activity, and binding assays known to those skilled in the art. Competitive inhibition assays can also be used.

Potential antagonists include small organic molecules, peptides, polypeptides and antibodies that bind to nucleic acid molecules coding for DbpA-derived protein or peptide fragments and thereby inhibit their activity or bind to a binding molecule (such as collagen to prevent the binding of the DbpA nucleic acid molecules or proteins to its ligand. For example, a compound that inhibits DbpA activity may be a small molecule that binds to and occupies the binding site of the DbpA protein, thereby preventing binding to cellular binding molecules, to prevent normal biological activity. Examples of small molecules include, but are not limited to, small organic molecule, peptides or peptide-like molecules. Other potential antagonists include antisense molecules. Preferred antagonists include compounds related to and variants or derivatives of the DbpA proteins or portions thereof. The nucleic acid molecules described herein may also be used to screen compounds for antibacterial activity.

The invention further contemplates a kit containing one or more DbpA-specific nucleic acid probes, which can be used for the detection of decorin-binding proteins from Borrelia in a sample, or for the diagnosis of Borrelia infections. Such a kit can also contain the appropriate reagents for hybridizing the probe to the sample and detecting bound probe. In an alternative embodiment, the kit contains antibodies specific to either or both the DbpA-derived protein or peptide fragments which can be used for the detection of Borrelia.

In yet another embodiment, the kit contains either or both the DbpA-derived protein or peptide fragments which can be used for the detection of Borrelia bacteria or for the presence of antibodies to decorin-binding DbpA proteins in a sample. The kits described herein may additionally contain equipment for safely obtaining the sample, a vessel for containing the reagents, a timing means, a buffer for diluting the sample, and a calorimeter, reflectometer, or standard against which a color change may be measured.

In a preferred embodiment, the reagents, including the protein or antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Peptide Map of DbpA. Overlapping synthetic peptides (P2–P9, SEQ IDS 3–10) (25 amino acids each) spanning the length of recombinant DbpA (underlined, SEQ ID 1) were constructed. Lysine modifications performed on mutants K14–K170 are indicated in bold.

FIG. 5. Blood and joint cultures from mice immunized with DbpA or DbpA-peptides. Blood (A) or joints (B) were taken from mice immunized as described in the legend for FIG. 4. Joints and 50 μl of blood were used to inoculate BSK II media 7 and 14 days post infection, respectively. The data are presented as percent positive cultures of 5 mice/group.

FIG. 7. Conserved lysine residues on DbpA. Conserved lysine residues were determined by protein sequence alignment of DbpA (strain 297) with DbpA sequences from various Borrelia genotypes (26). Bb, *B. burgdorferi;* Ba, *B. afzelii;* Bg, *B. garinii.* Numbers above the alignment indicate the numerical designation of each mutant when the corresponding lysine was mutated to alanine. Critical lysine residues involved in decorin binding are indicated in boldface.

FIG. 8. SDS-PAGE and Western ligand blot analysis of DbpA 549 and lysine modified proteins. Purified recombinant DbpA 549, OspC, and lysine mutants of DbpA were subjected to either SDS-PAGE (12%) under reducing conditions and stained with Coomassie brilliant blue (A) or transferred to a nitrocellulose membrane (B). The membrane was probed with digoxigenin-labeled decorin and visualized by alkaline phosphatase reactivity.

DESCRIPTION OF ILLUSTRATIVE EMBODIMENTS

Figure 2:
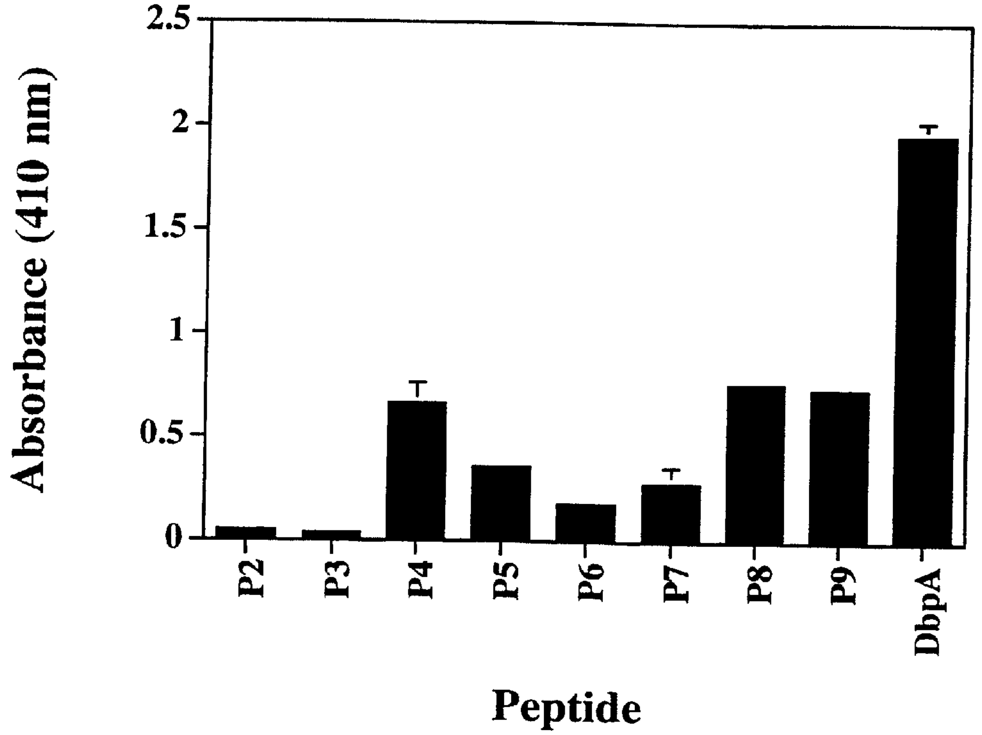
FIG. 2. Polyclonal Anti-DbpA serum recognizes individual DbpA-derived peptides. DbpA-peptides (2 μg/well) were probed with DbpA anti-serum. Data are expressed as O.D. 410 nm±SE of triplicate wells minus the substrate control.

Applicants discovered the efficacy of various DbpA-derived peptides. Three of the peptides selected (P4 (SEQ ID 5), P5 (SEQ ID 6), and P9 (SEQ ID 10)) contain lysine residues critical for decorin binding and were also recognized by serum raised against DbpA. Applicants further discovered that P4 (SEQ ID 5) and P5 (SEQ ID 6), which map to the K82 region of DbpA, are capable of inhibiting decorin attachment to DbpA-coated wells (64 and 92%, respectively). The K163/K170 peptide, P9 (SEQ ID 10), inhibited 43% and P2 (SEQ ID 3) showed an unexpected inhibition of 42%. This however, may be due in part to covalent interactions between the P2 (SEQ ID 3) cystine residue and decorin, which result in reduced binding. Applicants disclose that these peptides, with the exception of P2 (SEQ ID 3), bound to regions of DbpA critical for decorin binding. None of the lysine-modified peptides inhibit decorin binding, further substantiating the importance of lysine residues in this interaction.

Applicants assessed the DTH response to DbpA (SEQ ID 1) in peptide-immunized mice following the immunization/vaccination protocol in order to characterize, in vivo, peptide antigenicity. Applicants discovered that DbpA-immunized mice develop significant inflammation compared to controls, and P5-(SEQ ID 6) and P4/P5-(SEQ ID 5/SEQ ID 6) immunized mice also develop significant responses compared to their lysine-modified equivalents and other control groups. P4-(SEQ ID 5)and P9-(SEQ ID 10) immunized mice also develop a response greater than that of control groups but with less intensity and P2-(SEQ ID 3) immunized mice developed no response.

Applicants additionally disclose the ability of the peptides to confer protection against infection with low-passage *B. burgdorferi* by culturing blood (day 7 post infection) and joints (day 14 post infection) for the presence of spirochetes. The contralateral joint was also harvested for histological analysis. Blood analysis revealed that mice immunized with all DbpA peptides with the exception of P2 had fewer positive cultures (0–20 positive) compared to controls and DbpA-immunized mice (50–60% positive). These mice developed a more vigorous T cell response and/or have a higher concentration of protective antibodies than DbpA-immunized mice at this time point. The DbpA-immunized mice required more time to develop a response capable of controlling the disseminating Borrelia, as seen in part by joint cultures taken 14 days post infection. In these tissues, 20% of DbpA- and P4/P5-immunized mice and 60% of joints from P5-immunized mice were positive for Borrelia when compared to joints from the other groups (100% positive).

Arthritis incidence and severity was lowest in mice immunized with DbpA (SEQ ID 1), P4/P5 (SEQ ID 5/SEQ ID 6) and P5 (SEQ ID 6). This correlated somewhat with the number of Borrelia-positive joints and the DTH response in mice immunized with these formulations.

It is a matter of debate whether cellular or humoral immunity is protective against Borrelia infection (7, 23, 26–29) and many factors regarding the development of the immune response are affected by the nature of the infection (tick versus needle inoculation) (30, 31). *B. burgdorferi* is capable of invading a plethora of tissues and organs. It is conceivable that different types of immune responses may be beneficial, detrimental, or have no effect on the host depending on the stage of Borrelia dissemination and the tissue(s) involved. DbpA and the DbpA-peptides may drive the development of humoral/cellular immunity against Borrelia with different efficiency and intensity, which accounts for some of the variability in the numbers of positive cultures observed following immunization among the different groups.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Mice

Specific-pathogen free female C3H/HeJ ($MTV^-$) mice were purchased from Harlan Sprague Dawley (Houston, Tex.). The animals were maintained in facilities approved by the American Association for Accreditation of Laboratory Animal Care in accordance with current regulations and standards of the United States Department of Agriculture, Department of Health and Human Services, and the National Institutes of Health. The Institutional Animal Care and Use Committee approved all animal procedures. Female mice were 8–10 weeks old at the start of each experiment.

Synthesis of DbpA-peptides

Peptides (FIG. 1) were synthesized by a solid phase method on a p-benzyloxybenzyl alcohol resin using 9-fluorenylmethoxycarbonyl (Fmoc) chemistry and a model 396 Multiple Peptide synthesizer from Advanced Chem Tech Inc. (Louisville, Ky.) as described previously (21). Peptides were analyzed by reverse-phase HPLC on a Waters 625 Liquid Chromatography system using a $C_{18}$ analytical column. The purity of the peptides as assessed by HPLC was greater than 90% (21). Modification of lysine residues on DbpA-peptides resulting in P2 Mod-P9 Mod were performed as described (20).

Specificity of DbpA Anti-Serum for DbpA-peptides

Immulon-1 microtiter plate wells (Dynatech Labs, Chantilly, Va.) were coated with 2.0 μg of each peptide in 50 μl of PBS overnight at 4° C. The wells were washed and then blocked with 400 μl of Super Block (Pierce, Rockford, Ill.). All incubations were done at 37° C. and all dilutions were made using Super Block. After washing, 100 μl of a 1:1000 dilution of polyclonal, rabbit anti-DbpA (625) (17) was added for 1 hr. After washing, 100 μl of a 1:1000 dilution of AP-conjugated anti-rabbit IgG (Bio-Rad, Hercules, Calif.) was added for 1 hr. The wells were washed and incubated with 100 μl of a 1 mg/ml of Sigma 104 phosphatase substrate (Sigma Chemical Co., St. Louis, Mo.) dissolved in 1 M diethanolamine, 0.5 mM $MgCl_2$, pH 9.8. Plates were washed with 0.05% PBS-Tween 20 between all steps. The absorbance at 410 nm was determined in a Microplate Reader (Molecular Devices, Menlo Park, Calif.).

Attachment Inhibition Using DbpA-derived Peptides

Immulon-1 microtiter plate wells were coated with 0.4 μg of DbpA in 50 μl of PBS over night at 4° C. The wells were washed and then blocked as described above. During the blocking step, 0.12 μg/ml of biotin-conjugated decorin was pre-incubated at 37° C. with 5 μg of each DbpA-derived peptide or DbpA. After washing, 100 μl of the biotin conjugated decorin/inhibitor mixture was added to the wells and incubated for 1 h. After washing, the wells were incubated with AP-conjugated streptavidin and developed as described above.

Immunization of Mice with DbpA-derived Peptide

Mice were immunized with recombinant DbpA (SEQ ID 1), P2 (SEQ ID 3), P4 (SEQ ID 5), P5 (SEQ ID 6), P4/P5 (SEQ ID 5/SEQ ID 6), P9 (SEQ ID 10), or the corresponding lysine modified counterparts (P2 Mod, P4 Mod, P5 Mod or P9 Mod) using the immunization schedule established by Hanson (11). Briefly, mice were immunized with 20 μg of protein or peptide in complete Freund's adjuvant (CFA) (Week 1), boosted at week 4 with the same dose in incomplete Freund's adjuvant (IFA) and infected at week 6.

Bacterial Strains

Low-passage *B. burgdorferi* strain B31 (passage 5) was used in this study and cultured in BSK II (Barbour-Stoenner-Kelly) medium at 34° C. (22). Bacterial cultures were incubated in $CO_2$-enriched atmosphere in a GasPak chamber (BBL, Baltimore, Md.) containing BBL GasPak Plus envelopes and a GasPak anaerobic indicator (Beckton dickinson, Cockeysville, Md.) until the cells reached log phase. Bacterial counts were determined using dark field microscopy and a Petroff-Hausser chamber.

*Escherichia coli* strain JM101 (Qiagen, Chatsworth, Calif.) were grown at 37° C. in Lennox broth (LB) (Difco, Detroit, Mich.), containing the appropriate antibiotics.

Human fibroblast skin cells (ATCC #CRL-1475) were cultured on 16-well chamber slides (Nunc, Naperville, Ill.) in Dulbecco's Modified Essential Media containing 10% fetal bovine serum (DMEM) at 37° C.

Experimental Borrelia Infection

Mice (15 mice/group) were anesthetized with Metofane (methoxyflurane; Pitman-Moore, Mundelein, Ill.) and 10 mice/ group were infected i.d. at the base of the tail with $10^4$ Borrelia in 100 μl of media 6 six weeks after the first immunization. The remaining 5 mice/group were tested for a DTH response to recombinant DbpA. Following infection, mice were bled 7 and 14 days postinfection. Serum was collected for antibody analysis and blood cultured for the detection of live spirochetes by inoculating 5 ml of BSK II medium with 50 μl of blood from each infected mouse and cultured for 2 weeks at 34° C. as described above. Also on day 14 postinfection, mice were sacrificed and one hind tibiotarsal joint, heart, bladder, and a 3 mm skin biopsy from the ear were aseptically removed and inoculated into separate tubes containing 6 ml of BSK II medium with antibiotics (50 μg/ml rifampacin and 100 μg/ml phosphomycin (Sigma), and incubated for 2 weeks at 34° C. as described above. Evidence of arthritis was determined by histopathological examination of formalin-fixed hind tibiotarsal joint samples.

Delayed-type Hypersensitivity (DTH) to DbpA

Native C3H/HeJ mice immunized with DbpA (SEQ ID 1), P2 (SEQ ID 3), P4 (SEQ ID 5), P5 (SEQ ID 6), P4/P5 (SEQ ID 5/SEQ ID 6), P9 (SEQ ID 10), or the corresponding lysine modified counterparts (P2 Mod, P4 Mod, P5 Mod or P9 Mod) were challenged with 2 μg of recombinant DbpA in PBS (50 μl/footpad) 7 weeks after the initial immunization. All footpads were measured before and 24 h after challenge using a spring-loaded micrometer (Mitutoyo, Tokyo, Japan) as described (23). The mice were anesthetized as described above during footpad measurements and injections. Swelling was determined by subtracting the footpad measurements before challenge from those taken 24 h after challenge.

Arthritis Assessment

Evidence of arthritis was determined by histopathological examination of formalin-fixed hind tibiotarsal joint samples. Tissues for histological examination were embedded in paraffin and stained with hematoxylin and eosin. All sections were examined without knowledge of the vaccination status of the mouse. Arthritis was scored by one of two methods. A positive/negative assessment was used, as well as assignment of an arthritis severity score. Joints were scored according to the levels of infiltrate (neutrophils) as follows: 0, no arthritis, 1, minimal or rare (≦10% tissue involvement); 2, mild (10–20%); frequent (20–50%); and 4, severe (>50%).

Labeling of Decorin

Decorin from bovine fetal skin was purified and stored in 4 M guanidine hydrochloride at −80° C. and dialyzed extensively against PBS before use. Decorin was labeled with digoxigenin-3-O-methylcarbonyl-ϵ-aminocaproic acid-N-hydroxy-succinimide ester (digoxigenin) (Boehringer Mannheim, Indianapolis. Ind.) according to the manufacturer's instructions and stored at −20° C. To label decorin with biotin, 7.5 mg of NHS-LC-Biotin (sulfosuccinimidyl-6-(biotinamido) hexanoate) (Pierce, Rockford, Ill.) was dissolved in 100 μl of dimethyl sulfoxide and combined with 0.5 mg of decorin and 0.5 ml of 0.2 M sodium borate (pH 8.0) in a total reaction volume of 1 ml.

Construction of Expression Plasmids and Site-Directed Mutagenesis

DbpA was constructed using polymerase chain reaction (PCR). DbpA lysine mutants K14–K170 were constructed using extension overlap PCR and involved single lysine to alanine substitutions of the residues indicated in FIG. 7. Oligonucleotides used for PCR, listed in Table II, were purchased from Life Technologies, Inc. (Gaithersburg, Md.). Lysine to alanine verification for each mutant was analyzed by nucleotide sequencing with the Sequenase version 2.0 sequencing kit (US Biochemicals).

Expression and Purification of Recombinant Proteins

Recombinant DbpA, OspC (outer surface protein) and DbpA site-directed mutants from *B. burgdorferi* strain 297 were expressed in *E. coli* (JM 101) harboring the appropriate plasmid. *E. coli* was grown in LB until they reached an $A_{600}$ of 0.6. Isopropyl-β-D-thiogalactopyranoside (IPTG) (Life Technologies) was added to a final concentration of 0.2 mM, and the cells were incubated at 37° C. for an additional 4 hours. Cells from a 1 L culture were harvested by centrifugation and resuspended in 10 ml "binding buffer" (BB) (20 mM Tris HCl, 0.5 M NaCl, 15 mM imidazole, pH 8.0) and lysed in a French pressure cell at 11,000 pounds/inch$^2$. The lysate was centrifuged at 40,000×g for 15 min and the supernatant filtered through a 0.45 μm filter. A 1 ml iminodiacetic acid Sepharose column (Sigma, St. Louis, Mo.) was charged with 75 mM $NiC1_2.6H_{20}$ and equilibrated with BB. The filtered supernatant was applied to the column and washed with 10 volumes of BB, then 10 volumes of BB containing 60 mM imidazole. The bound proteins were eluted with BB containing 200 mM imidazole, dialyzed against PBS containing 10 mM EDTA, then dialyzed against PBS. The protein concentration was determined by the Bicinchoninic Acid (BCA) Protein Assay (Pierce) and proteins were stored at −20° C.

SDS-PAGE, Western Ligand Blots and Western Blot

Proteins (purified DbpA, DbpA site-directed mutants and OspC) were subjected to SDS-PAGE (reducing conditions) and probed with rabbit anti-DbpA polyclonal sera (R625) or with digoxigenin-labeled decorin.

Binding of Decorin to DbpA and DbpA Mutants

Immulon-1 microtiter plate wells (Dynatech Labs, Chantilly, Va.) were coated with 0.4 μg of DbpA (SEQ ID 1), DbpA mutants and K-mod in 50 μl PBS overnight at 4° C. The wells were washed and then blocked with 200 μl of Super Block (Pierce) for 1 h. After washing, 0.12 μg/ml of biotin-conjugated decorin in 100 μl of Super Block was added to the wells and incubated for 1 h. After washing, 100 μl of a 1:10,000 dilution of alkaline phosphatase (AP)-conjugated streptavidin (1 U/ml) (Boehringer Mannheim) was added and incubated for 1 h. The wells were washed and incubated for 30 min with 100 μl of a 1 mg/ml Sigma 104 phosphatase substrate (Sigma) dissolved in 1 M diethanolamine, 0.5 mM $MgCl_2$, pH 9.8. Plates were washed 4 times with PBS-0.05% Tween 20 between all steps and all incubations took place at 37° C. unless otherwise specified. All dilutions were made using Super Block. The absorbance was determined in a Microplate Reader (Molecular Devices, Menlo Park, Calif.).

Inhibition of DbpA Decorin Binding by DbpA Mutants

Immulon-1 microtiter plate wells were coated with 0.4 μg of DbpA in 50 μl of PBS overnight at 4° C. The wells were washed and then blocked as described above. Biotin-conjugated decorin (100 μl of 0.12 μg/ml solution) was pre-incubated at 37° C. with various amounts (1.0, 0.5, 0.25, 0.12 and 0.0625 μg/well) of unlabeled DbpA, DbpA site-specific mutants, or K-mod. After washing, 100 μl of the biotin-conjugated decorin/inhibitor mixture was added to the wells and incubated for 1 h. After washing, the wells were incubated with streptavidin AP and developed as described above. All dilutions were made using Super Block.

Attachment *B. burgdorferi* to Decorin Substrates Anal Inhibition by Recombinant Proteins Immulon-1 microtiter plate wells were coated with 1.0 μg of decorin in 50 μl PBS overnight at 4° C. After washing and blocking as described above, 0.5 μg of inhibitor protein (DbpA, DbpA site-directed mutants, K-mod, or OspC) were added per well in 50 μl of Super Block and incubated for 1 h. Subsequently, $4\times10^6$ Borreliae were added to each well in 50 μl of Super Block and the bacteria were allowed to attach to the substrate for 1 h at 37° C. as described previously (9). After washing, 100 μl of a 1:500 dilution of monoclonal mouse anti-OspA was added and incubated for 1 h. The wells were washed and incubated with 100 μl of a 1:3000 dilution of AP-conjugated goat anti-mouse IgG for 1 h. After washing, the wells were developed as described above. All incubations took place at 37° C. unless otherwise specified. All dilutions were made using Super Block.

Immunofluorescence

Human skin fibroblasts were cultured and fixed. Cells were plated onto 16-well chamber slides (Nunc) at a density of $2.5\times10^5$ cells per ml, grown for 2–3 days then fixed with −20° C. acetone and washed twice in PBS. All subsequent washes were done by immersing the slides in a staining dish filled with PBS 3 times, 10 minutes each wash unless otherwise specified. All incubations were done at room temperature. Unoccupied protein-binding sites on the slides were blocked with 80 μl of Super Block (Pierce) containing 1% goat and 5% horse serum (blocking buffer) (Life Technologies). The blocking buffer was carefully aspirated and 0.05 μg of DbpA, DbpA site-directed mutants, K-mod or the unrelated His-tag protein osteopontin (22) were added in 60 μl of blocking buffer for 20 min. After washing, 60 μl of a 1:500 dilution of rabbit anti-DbpA was added for 30 min. After washing, a final incubation with 60 μl of a 1:50 dilution of rhodamine-conjugated goat anti-rabbit IgG was added for 30 min in the dark. The slides were examined after washing using fluorescence microscopy. Photographs were taken at 20×magnification using Fuji Film 1600 ASA slide film. Anti-DbpA and rhodamine-conjugated goat anti-rabbit IgG antibodies were adsorbed against CRL-1475 cells prior to use. An equal mixture of $1\times10^6$ sonicated and whole CRL 1475 fibroblasts in 300 μl of PBS were incubated end over end at 37° C. for 1 h with an equal volume of each antibody. Adsorbed antiserum was collected after centrifugation of each tube at 5000 rpm for 5 min.

All antibody and protein dilutions were made in blocking buffer. Controls included a) incubations with secondary antibody only, b) anti-DbpA+secondary antibody, and c) DbpA or osteopontin+secondary antibody.

Chemical Modification of Lysine and Arginine Residues

Chemical modification of lysine residues was performed by incubating 700 μl of DbpA (1 mg/ml) with 5.4 mg DL-glyceraldehyde and 37.8 mg sodium cyanoborohydride for 1.5 hours at room temperature followed by overnight dialysis at 4° C. in 2 L of 50 mM ammonium bicarbonate and 2 L of PBS (pH 7.5) twice each.

Arginine residues on DbpA were chemically modified. Briefly, 1 mg of DbpA (2 ml) was dialyzed against 0.2 M sodium borate (pH 9.0) overnight at 4° C. The dialyzed protein was transferred to an eppendorf tube and incubated in the dark at 37° C. with 0.05 M cyclohexanedione. DbpA was then passed through a 0.02 M sodium borate-primed PD-10 column (Amersham Pharmacia Biotech. Piscataway, N.J.) and four 0.5 ml aliquots were collected.

Circular Dichroism Spectroscopy

Purified recombinant proteins were dialyzed against PBS (pH 7.4) at a concentration of 50 μg per ml. Circular dichroism (CD) spectroscopy measurements were performed using a Jasco J720 spectropolarimeter calibrated with a 0.06% (w/v) 10-d-camphorsulfonic acid ammonium salt solution. Measurements were taken at room temperature in a 0.2 mm pathlength quartz cell. All far-UV (250 to 190 nm) spectra were acquired with a time constant of 1 s, a scan rate of 20 nm/min, and 4 scans accumulated and then averaged.

Antibodies

Rabbit antiserum R625 (BioDesign International, Kennebunkport, Me.) was raised against DbpA. Monoclonal IgG2a antibody against OspA (4.5 mg/ml) (BOR-018–48316) was purchased from Capricorn Products, Inc. (Scarborough, Me.). Rhodamine-conjugated goat affinity purified antibody (1 mg/ml) to rabbit IgG (whole molecule) and alkaline phosphatase-conjugated (enzyme activity 1191 U/ml) goat affinity purified antibody to murine IgG (whole molecule) were purchased from Cappel (Durham, N.C.).

EXAMPLES

Example 1

Recognition of DbpA-peptides by Anti-DbpA Serum

Immunizations utilizing peptide formulations require that immune responses to the peptide(s) result in recognition of native-protein epitopes. To determine if the DbpA peptides containing the lysine residues previously demonstrated to be critical for decorin binding were also antigenic (20), a panel of overlapping peptides 25 amino acids in length was constructed (FIG. 1) and probed with polyclonal anti-DbpA serum (17). Cross-reactivity of peptide epitopes with native protein was examined by ELISA. As demonstrated in FIG. 2, anti-DbpA serum recognized native DbpA and to a lesser extent peptides containing the lysine residues K82, K163, and K170 which we recently showed to be critical for decorin binding (P4 (SEQ ID 5), P5 (SEQ ID 6), P8 (SEQ ID 9), and P9 (SEQ ID 10)) (20), suggested that these peptide sequences may also be antigenic.

Example 2

Inhibition of Decorin Attachment by Synthetic Peptides

Figure 3:
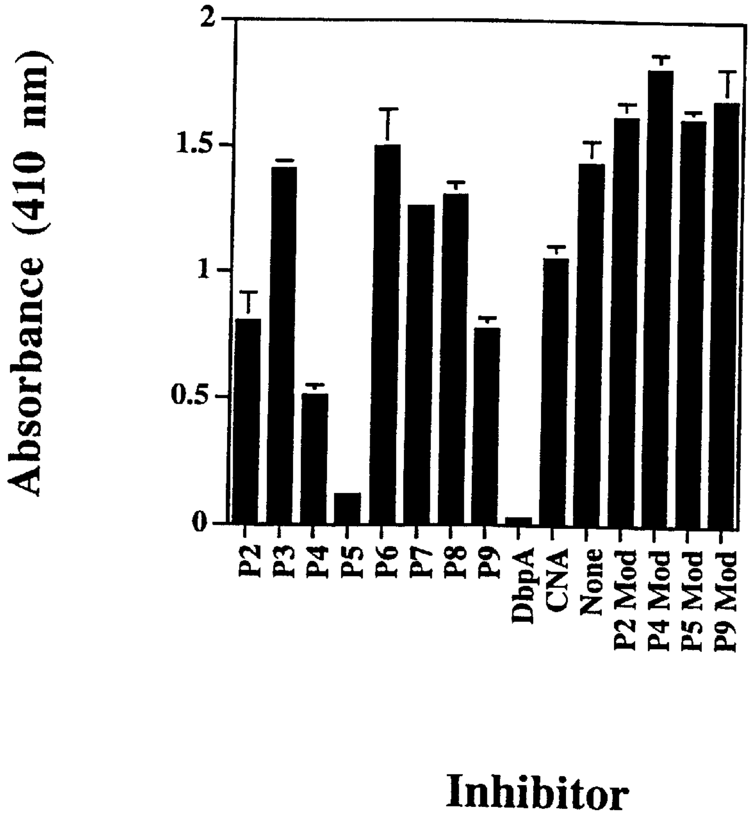
FIG. 3. Synthetic peptide inhibition of decorin binding. Biotin-conjugated decorin (0.006 μg) was pre-incubated with either 5 μg of DbpA (SEQ ID 1) or P2–P9 (SEQ IDS 3–10) for 1 hour and then added to DbpA-coated microtiter wells. The plate was developed and O.D. read at 410 nm. The data are expressed as ±SE of the mean of triplicate wells minus the substrate control. This experiment was performed 3 times with similar results.
Figure 4:
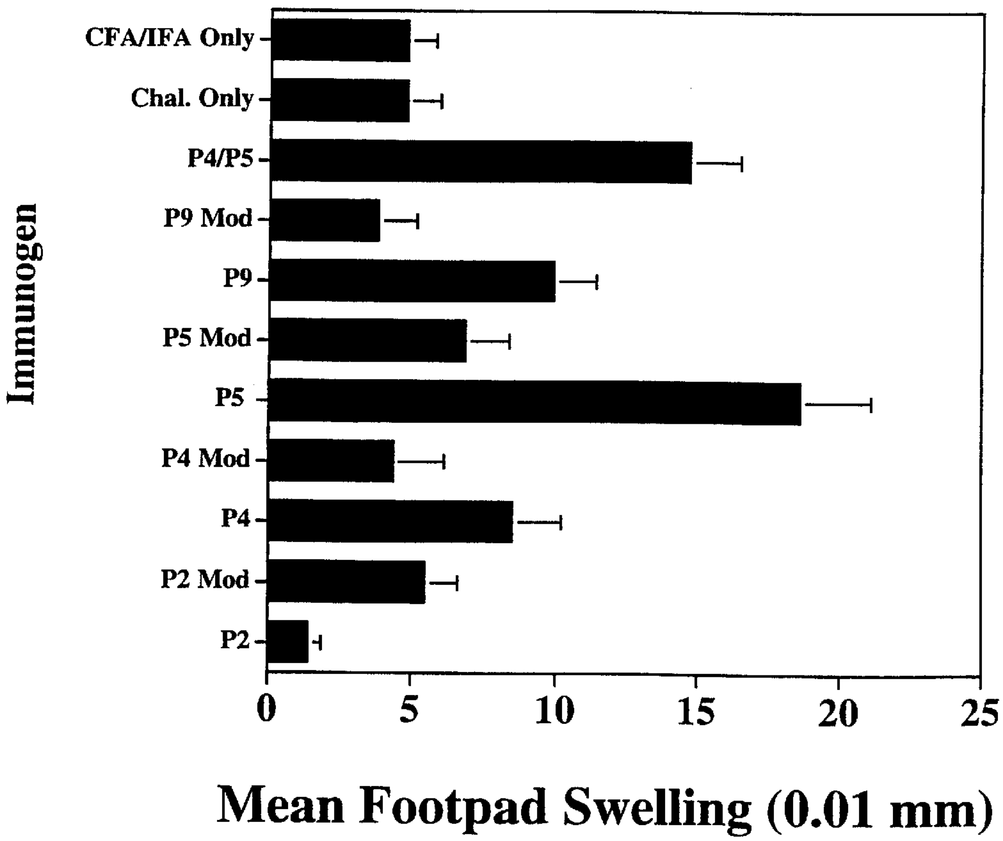
FIG. 4. DTH response to DbpA following immunization with DbpA-peptides. Mice were immunized with various peptide formulations or recombinant DbpA (SEQ ID 1). One week after the second immunization, mice were challenged with 2 μg of the noted peptide formulations or recombinant DbpA (50 μl). Specific footpad swelling was determined by subtracting the thickness of the footpad before challenge from the thickness measured 24 hours post challenge. The values are means±SE of 5 mice/group.

Confirmation of the critical binding sites in DbpA for decorin and of the biophysical stability of these peptides was tested in an inhibition ELISA. DbpA, peptides P2–P9, chemically modified peptides P2 Mod–P9 Mod, and an irrelevant peptide from the *Staphylococcus aureus* collagen-binding adhesin, CNA4 (OSKITVDNTKNTIDVTIQG) (SEQ ID 36) were used as inhibitors of decorin attachment to DbpA-coated wells. Peptides P4 (SEQ ID 5) and P5 (SEQ ID 6), which contain K82, demonstrated dramatic inhibitory effects (64 and 92%, respectively) when compared to the other peptides (FIG. 3). P9 (SEQ ID 10), which contains K163 and K170 moderately inhibited decorin binding (42%) and P2 (SEQ ID 3) inhibited binding by 44%.

Example 3

DTH Response to DbpA Following Peptide Immunization

DTH is an in vivo method of testing T cell-dependent immune responses that are manifested by inflammation at the site of antigenic challenge. Mice immunized with DbpA (SEQ ID 1), P2 (SEQ ID 3), P4 (SEQ ID 5), P5 (SEQ ID 6), P4/P5 (SEQ ID 5/SEQ ID 6) combined, P9 (SEQ ID 10), or the corresponding lysine-modified peptides were challenged in the footpad with 2 μg of recombinant DbpA (SEQ ID 1). Footpad measurements were taken before and after challenge as described above. DbpA (SEQ ID 1)-immunized mice developed a significant footpad swelling of 53.3±3.5 (not shown) compared to mice immunized with adjuvant alone or naive mice receiving only the DbpA (SEQ ID 1) challenge. Peptide-immunized mice, with the exception of P2 (SEQ ID 3), also developed a significant DTH response to DbpA (SEQ ID 1) compared to the lysine-modified controls. These data suggested that immunization with peptides containing the critical lysine residues involved in decorin binding had antigenic potential and could elicit a DTH response to native protein.

Example 4

DbpA-Peptides Confer Protection Against *B. burgdorferi* Infection

To test whether the various DbpA-peptides conferred protection against Borrelia infection, mice were immunized with DbpA, DbpA-peptides, or the lysine-modified DbpA-peptides and then infected as described above.

Seven days post infection blood was examined for the presence of spirochetes. Mice immunized with P4 (SEQ ID 5), P5 (SEQ ID 6), P4/P5 (SEQ ID 5/SEQ ID 6), or P9 (SEQ ID 10) had fewer positive cultures (<20%) when compared to P2-(SEQ ID 3), lysine-modified peptide-, DbpA (SEQ ID 1), or adjuvant-immunized controls (FIG. 5).

Figure 6:
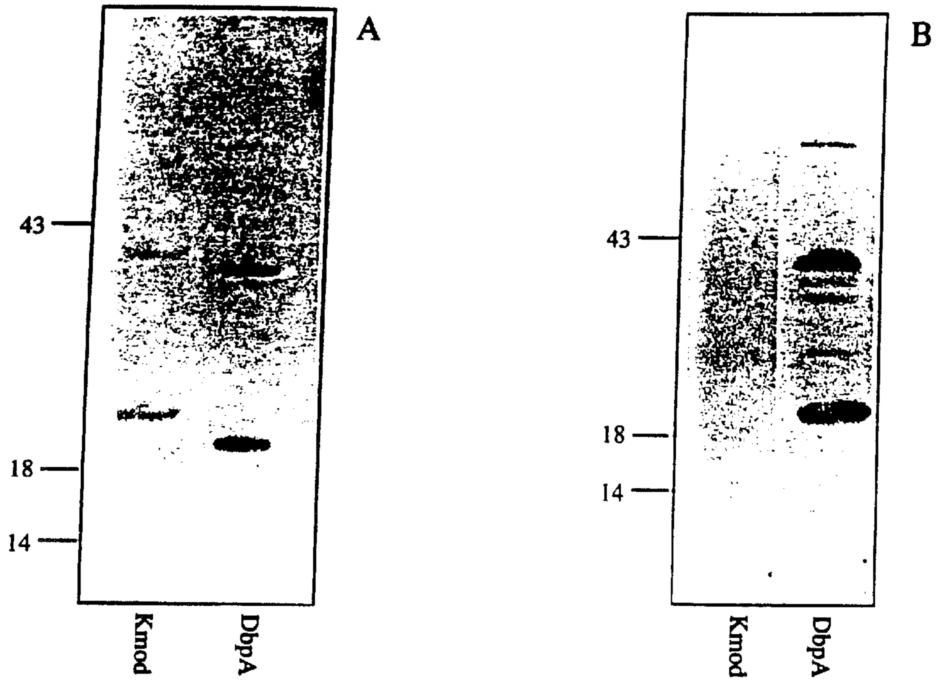
FIG. 6. SDS-PAGE and Western ligand blot analysis of DbpA and chemically modified DbpA (K-mod). Purified DbpA and K-mod were subjected to SDS-PAGE (12%) under reducing conditions and stained with Coomassie brilliant blue (A) or transferred to a nitrocellulose membrane (B). After blocking additional protein-binding sites, proteins on the membrane were probed with digoxigenin-labeled decorin and visualized by alkaline phosphatase reactivity.

Joints harvested 14 days post infection and cultured for the presence of spirochetes revealed that only DbpA-(SEQ ID 1), P4/P5-(SEQ ID 5/SEQ ID 6), and to a lesser extent P5-(SEQ ID 6) immunized mice had fewer positive cultures (20 and 60% respectively) when compared to the other treatment groups (100%) (FIG. 6).

A similar trend was also observed for joints examined for arthritis (Table I). DbpA-(SEQ ID 1), P4-(SEQ ID 5), and P5-(SEQ ID 6) immunized mice had the lowest arthritis ratings (0.2, 1.2, and 0.4, respectively) and lowest arthritis incidence (20, 60, and 20%, respectively). Mean arthritis scores were also low for P2 (SEQ ID 3), P9 (SEQ ID 10), and P4/P5 (SEQ ID 5/SEQ ID 6) (1.4, 1.25, and 1.6, respectively), however, the arthritis incidence in these groups was intermediate (approximately 80%) compared to 100% incidence in control groups with the exception of P9 Mod (80% incidence).

Example 5

Lysine Residues in Dbpa Participate in Decorin Binding

*B. burgdorferi* expresses two adhesins in the 20 kDa molecular weight range (DbpA and DbpB) of the MSCRAMM family which mediate the attachment of the spirochete to decorin and bind the proteoglycan with an estimated $K_D$ of approximately $10^{-7}$. DbpA binds decorin in both ELISA and Western ligand blot analysis. In addition, DbpA recognizes decorin in an organized extracellular matrix produced by cultured skin fibroblasts and mediates attachment of DbpA-coated beads to fibroblast cultures. To further characterize this interaction, residues within DbpA that are necessary for binding to decorin are identified.

Biotin conjugation to primary amino groups in DbpA results in loss of decorin binding activity, suggesting a role for lysine residues in this interaction. Further, the side chains of lysine residues were chemically modified and the binding properties of the resulting protein examined. Chemical substitution of the primary amino groups resulted in a DbpA form that migrated as a somewhat larger protein compared to unmodified DbpA when analyzed by SDS-PAGE (FIG. 6A). Both forms of DbpA migrated as two bands, monomers at 20 and 21 kDa and dimers at 40 and 42 kDa for DbpA and chemically modified DbpA (K-mod), respectively. The decorin binding activity of the DbpA and lysine-modified DbpA was examined in a Western ligand blot assay (FIG. 6B). Substitution of primary amino groups in DbpA resulted in loss of decorin binding, whereas unmodified DbpA transferred to a supporting membrane bound digoxigenin-labeled decorin. Chemical modification of arginine residues did not affect the ability of DbpA to bind decorin (data not shown).

Example 6

The Importance of Individual Lysine Residues for Decorin Binding

Lysine residues are critical for the decorin binding activity of DbpA. To evaluate the importance of individual lysine residues, selected residues were changed to alanine and decorin-binding activity of the resulting mutants was analyzed. Of the 27 lysine residues present in the native DbpA protein sequence, three are present in the leader sequence. The recombinant form of DbpA used in this study contained part of the leader sequence, including one of the lysine residues (K14). By comparing the DbpA sequences of various *B. burgdorferi* sensu lato strains to the DbpA sequence of *B. burgdorferi* 297 (FIG. 7), 5 lysine residues that were conserved in all 30 sequences examined (K32, K82, K104, K163, and K170) and 6 that were conserved in most DbpA sequences (K14, K40, K50, K51, K91, and K102) were identified. These residues shown in FIG. 7 were individually targeted for mutational analysis of recombinant DbpA of *B. burgdorferi* strain 297 using extension overlap PCR (FIG. 7). DbpA and all mutant proteins were expressed as N-terminal polyhistidine (His-tag) fusions and purified using nickel-chelating chromatography.

SDS-PAGE analysis of DbpA site-directed mutants (K14, K32, K40, and K163 are not shown) revealed no significant differences when compared to native DbpA (FIG. 8A). Circular dichroism (CD) spectroscopy showed that the overall secondary structure of DbpA and all site-directed mutants were nearly identical (data not shown), indicating that the mutations did not grossly alter the structure of the protein. Western ligand blot analysis, however, demonstrated that although all mutants were still recognized by anti-DbpA polyclonal antiserum (data not shown), mutants K82, K163 (not shown) and K170 lost their ability to bind decorin (FIG. 8B). Mutant K51 showed reduced decorin binding activity and a recombinant, unrelated His-tag protein OspC did not bind decorin (FIG. 8B).

Also examined was the ability of biotin-conjugated decorin to bind to different forms of DbpA-coated microtiter wells. The chemically modified DbpA (Kmod) was essentially unable to support the binding of decorin. The single lysine mutants K82, K163, and K170 bound significantly less decorin compared to the wild-type DbpA and the binding of decorin to K51 was marginally reduced.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Steere, A. C. 1989. Lyme Disease. *N. Engl. J. Med.* 9:586–596.
2. Burgdorfer, W., J. F. Anderson, R. S. Lane, J. Piesman, and A. Spielman. 1991. Relationship of *Borrelia burgdorferi* to its arthropod vectors. *Scand. J. Infect Dis. Suppl.* 77:35–40.

3. Benach, L. J., J. L. Coleman, R. A. Skinner, and E. M. Bosler. 1987. Adult *Ixodes dammini* on rabbits: a hypothesis for the development and transmission of *Borrelia burgdorferi*. *J. Infect. Dis.* 155: 1300–1306.

4. de Silva, A. M., and E. Fikrig. 1997. Arthropod and host-specific gene expression by *Borrelia burgdorferi*. *J. Exp. Med.* 99:377–379.

5. Montgomery, R. R., S. E. Malawista, K. J. M. Feen, and L. K. Bockenstedt. 1996. Direct demonstration of antigenic substitution of *Borrelia burgdorferi* ex vivo: exploration of the paradox of the early immune response to outer surface proteins A and C in Lyme disease. *J. Exp. Med.* 183:261–269.

6. Wormser, G. P., J. Nowakowski, R. B. Nadelman, I. Schwartz, D. McKenna, D. Holmgren, and M. Aguero-Rosenfeld. 1998. Efficacy of an OspA vaccine preparation for prevention of Lyme disease in New York state. *Infection.* 26:208–212.

7. Schaible, U. E., M. D. Kramer, K. Eichmann, M. Modolell, C. Museteanu, and M. M. Simon. 1990. Monoclonal antibodies specific for the outer surface protein A (OspA) of *Borrelia burgdorferi* prevent Lyme borreliosis in severe combined immunodeficiency (scid) mice. *Proc. Natl. Acad. Sci., U.S.A.* 87:3768–3772.

8. Fikrig, E., S. W. Barthold, D. H. Persing, X. Sun, F. S. Kantor, and R. A. Flavell. 1992. *Borrelia burgdorferi* strain 25015: charactenzation of outer surface protein A and vaccination against infection. *J. Immunol.* 148:2256–2260.

9. de Silva, A. M., S. R. T. III, L. R. Brunet, S. W. Barthold, and E. Fikrig. 1996. *Borrelia burgdorferi* OspA is an arthropod-specific transmission-blocking Lyme disease vaccine. *J. Exp. Med.* 183:271–275.

10. Cassatt, D. R., N. K. Patel, N. D. Ulbrandt, and M. S. Hanson. 1998. DbpA, but not OspA, is expressed by *Borrelia burgdorferi* during spirochetemia and is a target for protective antibodies. *Infect. Immun.* 66:5379–5387.

11. Hanson, M. S., D. R. Cassaft, B. P. Guo, N. K. Patel, M. P. McCarthy, D. W. Dorward, and M. Höök. 1998. Active and passive immunity against *Borrelia burgdorferi* decorin binding protein A (DbpA) protects against infection. *Infect. Immun.* 66:2143–2153.

12. Barthold, S. W., E. Fikrig, L. K. Bockenstedt, and D. H. Persing. 1995. Circumvention of outer surface protein A immunity by host-adapted *Borrelia burgdorferi*. *Infect. Immun.* 63:2255–2261.

13. Foley, D. M., Y. P. Wang, X. Y. Wu, D. R. Blanco, M. A. Lovrich, and J. N. Miller. 1997. Acquired resistance to *Borrelia burgdorferi* infection in the rabbit. Comparison between outer surface protein A vaccine-and infection-derived immunity. *J. Clin. Invest.* 99:2030–2035.

14. Lovrich, S. D., S. M. Callister, B. K. DuChateau, L. C. Lim, J. Winfrey, S. P. Day, and R. F. Schell. 1995. Abilities of OspA proteins from different seroprotective groups of *Borrelia burgdorferi* to protect hamsters from infection. *Infect. Immun.* 63:2113–2119.

15. Padilla, M. L., S. M. Callister, R. F. Schell, G. L. Bryant, D. A. Jobe, S. D. Lovrich, B. K. DuChateau, and J. R. Jensen. 1996. Characterization of the protective borreliacidal antibody response in humans and hamsters after vaccination with a *Borrelia burgdorferi* outer surface protein A vaccine. *J. Infect Dis.* 174:739–746.

16. Zhong, W., T. Stehle, C. Museteanu, A. Siebers, L. Gern, M. Kramer, R. Wallich, and M. M. Simon. 1997. Therapeutic passive vaccination against chronic Lyme disease in mice. *Proc. Natl. Acad. Sci. U.S.A.* 94: 12533–12538.

17. Guo, B. P., E. L. Brown, D. W. Dorward, L. C. Rosenberg, and M. Höök. 1998. Decorin binding adhesins from *Borrelia burgdorferi*. *Mol. Miro.* 30:711–723.

18. Guo, B., S. J. Norris, L. C. Rosenberg, and M. Höök. 1995. Adherence of *Borrelia burgdorferi* to the proteoglycan decorin. *Infect Immun.* 63:3467–3472.

19. Roberts, W. C., B. A. Mullikin, R. Lathigra, and M. S. Hanson. 1998. Molecular analysis of sequence heterogeneity among genes encoding decorin binding proteins A and B of *Borrelia burgdorferi* sensu lato. *Infect. Immune.* 66:5275–5285.

20. Brown, E. L., B. P. Guo, P. O'Neal, and M. Höök. 1999. Adherence of *Borrelia burgdorferi:* Identification of critical lysine residues in DbpA required for decorin binding. *J. Biol. Chem.* 274:26272–26278.

21. Patti, J. M., K. House-Pompeo, J. O. Boles, N. Garza, S. Gurusiddappa, and M. Höök. 1995. Critical residues in the ligand-binding site of the *Staphylococcus aureus* collagen-binding adhesin (MSCRAMM). *J. Biol. Chem.* 270:12005–12011.

22. Barbour, A. G. 1984. Isolation and cultivation of Lyme disease spirochetes. *Yale J. Biol Med.* 57:521–525.

23. Pride, M. W., E. L. Brown, L. C. Stephens, J. J. Killion, S. J. Norris, and M. L. Kripke. 1998. Specific Thl cell lines that confer protective immunity against experimental *Borrelia burgdorferi* infection in mice. *J. Leukoc. Biol.* 63:542–549.

24. Gross, D. M., T. Forsthuber, M. Tary-Lehmann, C. Etling, K. Ito, Z. A. Nagy, J. A. Field, A. C. Steere, and B. T. Hubber. 1998. Identification of LFA-1 as a candidate autoantigen in treatment-resistant Lyme arthritis. *Science.* 281: 703–706.

25. Francis, M. J. 1996. Synthetic Peptides. In Vaccine Protocols. A. Robinson, G. H. Farrar, and C. N. Wiblin, editors. Humana Press, Totowa. 75–90.

26. Keane-Myers, A., and S. P. Nickell. 1995. T cell subset-dependent modulation of immunity to *Borrelia burgdorferi* in mice. *J. Immunol.* 154: 1770–1776.

27. Lengl-Janssen, B., A. F. Strauss, A. C. Steere, and T. Kamradt. 1994. The T helper cell response in Lyme arthritis: Differential recognition of *Borrelia burgdorferi* outer surface protein A in patients with treatment-resistant or treatment-responsive Lyme arthritis. *J. Exp. Med.* 180:2069–2078.

28. Rao, T. D., and A. B. Frey. 1995. Protective resistance to experimental *Borrelia burgdorferi* infection of mice by adoptive transfer of a CD4+ T cell clone. *Cell. Immunol.* 162:225–234.

29. Schaible, U. E., M. D. Kramer, R. Wallich, T. Tran, and M. M. Simon. 1991. Experimental *Borrelia burgdorferi* infection in inbred mouse strains: andbody response and association of H-2 genes with resistance and susceptibility to development of arthritis. *Eur. J. Immunol* 21:2397–2405.

30. Zeidner, N., M. Dreitz, D. Belasco, and D. Fish. 1996. Suppression of acute *Ixodes scapularis*-induced *Borrelia burgdorferi* infection using tumor necrosis factor-α, interleukin-2, and interferon-γ *J. Infec. Dis.* 173:187–195.

31. Zeidner, N., M. L. Mbow, M. Dolan, R. Massung, E. Baca, and J. Piesman. 1997. Effects of *Ixodes scapularis* and *Borrelia burgdorferi* on modulation of the host immune response: induction of a TH2 cytokine response in Lyme disease-susceptible (C3H/HeJ) mice but not in disease-resistant (Balb/c) mice. *Infect. Immun.* 65:3100–3106.

32. VanMierlo, P., Jacob, W., and Docks, P. (1993) *Dermatol.* 186, 306–310

33. Duray, P. H. (1992) in *Lyme Disease: Molecular and Immunologic Approaches* (Schutzer, S. E., ed), pp. 11–30, Cold Spring Harbor Laboratory Press, Plainview, N.Y.

34. Sambri, V., Aldini, R., Massaria, F., Montagnani, M., Casanova, S., and Cevenini, R. (1996) *Infect Immun.* 64, 1858–1861
35. Barthold, S. W., Souza, M. S. d., Janotka, J. L., Smith, A. L., and Persing, D. H. (1993) *Am. J. Pathol.* 143, 959–971

TABLE I

Arthritis Development in C3H/Hen Mice Immunized with DbpA and Various DbpA Peptides

| Immunogen | % Incidence | Mean Arthritis Rating |
|---|---|---|
| Infection only | 100 | 3.6 |
| CFA only | 100 | 2.25 |
| DbpA | 20 | 0.2 |
| P2 | 80 | 1.4 |

TABLE I-continued

Arthritis Development in C3H/Hen Mice Immunized with DbpA and Various DbpA Peptides

| Immunogen | % Incidence | Mean Arthritis Rating |
|---|---|---|
| P2 Mod | 100 | 1.8 |
| P4 | 60 | 1.2 |
| P4 Mod | 2.0 | 2.0 |
| P5 | 20 | 0.4 |
| P5 Mod | 100 | 3.2 |
| P9 | 75 | 1.25 |
| P9 Mod | 80 | 2.0 |
| P4/P5 | 60 | 1.6 |
| Joint only | 0 | 0.0 |

TABLE II

Primers used to construct DbpA 549 and the DbpA Lysine Mutants

| Protein | Forward Primer(s) |
|---|---|
| DbpA SEQ ID 11 | (BN1OF2),5'-CGCGGATCCAACAATTTACTTAAACTA-3' |
| K14 SEQ ID 13 | 5'-CGCGGATCCAACTTTTAACAATTTACTTGCACTAACTAT-3' |
| K32† SEQ ID 14 | 5'-AACAGGAGCAACAGCAATCAAATTAGAATCATCAGCTAAA-3' |
| K40† SEQ ID 16 | 5'-AATTAGAATCATCAGCTAGCGCCATTGTAG-3' |
| K50† SEQ ID 18 | 5'-AGATGCAATTGCAAAAAAGGCloCT-3' |
| K50† SEQ ID 20 | 5'-AGATGCAATTGCAGCAGCGGCTGCTT-3' |
| K51† SEQ ID 22 | 5'-AGATGCAATTGCAGCAGCGGCTGCTT-3' |
| K82† SEQ ID 24 | 5'-ATACTTGAAGCAGCAGTGCGAGCT-3' |
| K91† SEQ ID 26 | 5'-TAGCGGAAGCATTCGTAA-3' |
| K102† SEQ ID 28 | 5'-AAGCTACTGCACTTAAAGAAACTGG-3' |
| K104† SEQ ID 30 | 5'-AAGCTACTAAACTTGCAGAAACTGG-3' |
| K163† SEQ ID 32 | 5'-AAAATGAGAGAAGCATTACAAAGGGT-3' |
| K170† SEQ ID 34 | 5'-TTCACAAGGCAAACCAAGACA-3 |

| Protein | Reverse Primer(s) |
|---|---|
| DbpA SEQ ID 11 | (EndP)5'-GCCCTGCAGTTACGA m AGCAGTGCT-3' SEQ ID 12 |
| K14 SEQ ID 13 | End P |
| K32† SEQ ID 14 | 5'-TTTAGCTGATGATTCTAATTTGATTGCTGTTGCTCCTGTT-3' SEQ ID 15 |
| K40† SEQ ID 16 | 5'-CTACAATGGCGCTAGCTGATGATTCTAATT-3' SEQ ID 17 |
| K50† SEQ ID 18 | 5'-AGCAGCCTTTTTTGCAATTGCATCT-3' SEQ ID 19 |
| K50† SEQ ID 20 | 5'-AAGCACCCGCTOCTGCAATTGCATCT-3' SEQ ID 21 |
| K51† SEQ ID 22 | 5'-AAGCAGCCGCTGCTGCAATTGCATCT-3' SEQ ID 23 |
| K82† SEQ ID 24 | 5'-AGTAGCTCGCACTGCTGCTTCAAG-3' SEQ ID 25 |
| K91† SEQ ID 26 | 5'-TTACGAATCCTTCCGCAA-3' SEQ ID 27 |
| K102† SEQ ID 28 | 5'-CCAGTTTCTTTAAGTGCAGTAGCT-3' SEQ ID 29 |
| K104† SEQ ID 30 | 5'-CCAGTTTCTGCAAGTTTAGTAGCTT-3' SEQ ID 31 |
| K163† SEQ ID 32 | 5'-ACCCTTTGTAATGCTTCTCTCATTTT-3' SEQ ID 33 |
| K170† SEQ ID 34 | 'S'-TGTCTTGGTTTGCCTTGTGAA-3' SEQ ID 35 |

†BIOF2 and EndP were also used in the formation of this mutant.

What is claimed is:

1. A method of generating an immune response against Borrelia bacteria comprising administering an effective amount of a peptide or a combination of two or more peptides selected from the group consisting of SEQ ID NO: 3, SEQ ID NO: 5, SEQ ID NO: 6, and SEQ ID NO: 10.

2. A method according to claim 1, wherein the peptide is administered to a mammal.

3. A method according to claim 1, wherein the peptide or combination of peptides is selected from the group consisting of SEQ ID NO: 5 and SEQ ID NO: 6.

* * * * *